US009243494B2

United States Patent
van Zuilekom et al.

(10) Patent No.: US 9,243,494 B2
(45) Date of Patent: Jan. 26, 2016

(54) APPARATUS AND METHOD FOR FLUID PROPERTY MEASUREMENTS

(71) Applicant: Halliburton Energy Services, Inc., Houston, TX (US)

(72) Inventors: Anthony H. van Zuilekom, Houston, TX (US); Mark A. Proett, Missouri City, TX (US); Bruce H Storm, Jr., Houston, TX (US); George Kveton, Benbrook, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 14/283,658

(22) Filed: May 21, 2014

(65) Prior Publication Data

US 2014/0332280 A1    Nov. 13, 2014

Related U.S. Application Data

(62) Division of application No. 12/673,686, filed as application No. PCT/US2008/006045 on May 9, 2008, now Pat. No. 8,775,089.

(60) Provisional application No. 60/965,351, filed on Aug. 20, 2007.

(51) Int. Cl.
  *E21B 49/08* (2006.01)
  *G01N 9/00* (2006.01)

(52) U.S. Cl.
  CPC .............. *E21B 49/088* (2013.01); *E21B 49/08* (2013.01); *G01N 9/00* (2013.01)

(58) Field of Classification Search
  None
  See application file for complete search history.

(56) References Cited

U.S. PATENT DOCUMENTS

| | | |
|---|---|---|
| 4,763,730 A | 8/1988 | Suzuki |
| 6,178,815 B1 | 1/2001 | Felling et al. |
| 6,218,662 B1 | 4/2001 | Tchakarov et al. |
| 7,458,257 B2 | 12/2008 | Pop et al. |
| 2004/0000636 A1 | 1/2004 | Mullins et al. |
| 2005/0242807 A1 | 11/2005 | Freedman |
| 2006/0101905 A1* | 5/2006 | Bittleston et al. .......... 73/152.24 |
| 2006/0243047 A1* | 11/2006 | Terabayashi et al. ...... 73/152.55 |

(Continued)

FOREIGN PATENT DOCUMENTS

| | | |
|---|---|---|
| GB | 2407109 A | 4/2005 |
| WO | WO-01/51898 A1 | 7/2001 |

(Continued)

OTHER PUBLICATIONS

"U.S. Appl. No. 12/673,686, Advisory Action mailed Dec. 30, 2013", 3 pgs.

(Continued)

*Primary Examiner* — Aditya Bhat
(74) *Attorney, Agent, or Firm* — Schwegman Lundberg & Woessner, P.A.; Benjamin Fite

(57) ABSTRACT

In some embodiments, apparatus and systems, as well as methods, may operate to measure formation fluid and obtain data, the data having measurement levels that vary over a parameter. The data is grouped in one or more categories, each category having data falling within a range, and the grouped data is analyzed as a function of the parameter. In some embodiments, the grouped data is used to identify at least one fluid type of the formation fluid using the grouped data.

6 Claims, 25 Drawing Sheets

(56) References Cited

U.S. PATENT DOCUMENTS

| | | |
|---|---|---|
| 2007/0035736 A1 | 2/2007 | Vannuffelen et al. |
| 2007/0119244 A1 | 5/2007 | Goodwin et al. |
| 2011/0048700 A1 | 3/2011 | van Zuilekom et al. |

FOREIGN PATENT DOCUMENTS

| | | |
|---|---|---|
| WO | WO-2006/063094 A1 | 6/2006 |
| WO | WO-2009-025688 A1 | 2/2009 |

OTHER PUBLICATIONS

"U.S. Appl. No. 12/673,686, Final Office Action mailed Oct. 11, 2013", 9 pgs.

"U.S. Appl. No. 12/673,686, Non Final Office Action mailed Jun. 18, 2013", 8 pgs.

"U.S. Appl. No. 12/673,686, Notice of Allowance mailed Feb. 20, 2014", 9 pgs.

"U.S. Appl. No. 12/673,686, Response filed Jan. 27, 2014 to Advisory Action mailed Dec. 30, 2013 and Final Office Action mailed Oct. 11, 2013", 8 pgs.

"U.S. Appl. No. 12/673,686, Response filed May 29, 2013 to Restriction Requirement mailed Apr. 29, 2013", 5 pgs.

"U.S. Appl. No. 12/673,686, Response filed Sep. 18, 2013 to Non Final Office Action mailed Jun. 18, 2013", 9 pgs.

"U.S. Appl. No. 12/673,686, Response filed Dec. 10, 2013 to Final Office Action mailed Oct. 11, 2013", 9 pgs.

"U.S. Appl. No. 12/673,686, Restriction Requirement mailed Apr. 29, 2013", 8 pgs.

"Application Serial No. PCT/US2008/006045, International Search Report and Written Opinion mailed Oct. 8, 2008", 12 pgs "European Applicaiton Serial No. 08767668.0, Office Action mailed Nov. 24, 2010", 4 pgs.

"European Application Serial No. 08767668.0, Response filed Mar. 10, 2011 to Office Action mailed Nov. 24, 2010", 11 pgs.

Thomas, O. O. A., "The Data as the Model: Interpreting Permanent Downhole Gauge Data Without Knowing the Reservoir Model", Masters Thesis, submitted to the Department of Petroleum Engineering of Stanford University, (Jun. 2002), 48 pgs.

"Application Serial No. 2008/11272, First Examination Report mailed Jun. 2, 2014", 4 pgs.

"Application Serial No. 2008/11272, Request for Re-Examination filed Sep. 10, 2014 in response to First Examination Report mailed Jun. 2, 2014", 1 pg.

"European Application Serial No. 08767668.0, Examination Notification Art. 94(3) mailed Dec. 2, 2014", 3 pgs.

* cited by examiner

APPARATUS AND METHOD FOR FLUID PROPERTY MEASUREMENTS

RELATED APPLICATIONS

This application is a divisional of U.S. patent application Ser. No. 12/673,686, filed Nov. 11, 2010 which is a nationalization under 35 U.S.C. 371 of PCT/US2008/006045, filed May 9, 2008, and published as WO 2009/025688 A1 on Feb. 26, 2009, which claims priority to U.S. Provisional Patent Application Ser. No. 60/965,351, filed Aug. 20, 2007; which applications and publication are incorporated herein by reference in their entirety and made a part hereof.

TECHNICAL FIELD

Various embodiments described herein relate to determining characteristics of geological formations, including density and porosity.

BACKGROUND

In the process of exploration and development of hydrocarbons, wells are drilled using drilling fluids. These drilling fluids are composed of liquids that are weighted with fine grained solids like barite which increases the density of the drilling fluids to exceed the pressure of the fluids in the formation rock pores. This keeps the formation fluid in place while drilling and prevents the formations fluids from being produced to the surface in an uncontrollable manner which is commonly know as a blowout. Since the pressure of the mud system exceeds the formation pore pressure the mud fluids (know as filtrate) will flow into the formation. This process is called invasion. The mud systems are designed to minimize this invasion by forming a mud cake composed of the solids being deposited on the well bore walls. It is desirable to obtain formation samples to prove the existence of producible hydrocarbons in the rock pores. In a down hole fluid sampling process, the primary objective is to obtain or identify formation samples representative of true, for example, clean formation fluid or native fluid with a low contamination level of borehole fluids or drilling fluids.

During the pumping process, physical and chemical properties of formation fluids being extracted from the formation can be measured using sensors placed along the flowline of the tool. The sensor measurements are used to try and identify the fluid type, and to calculate the contamination level.

The pumped fluids usually consist of a mixture that is segregated where a single measurement in time cannot be made that accurately represents the bulk fluid mixture, and the data measurements are erratic. While an average of the data can be made, the average of the data often fails to accurately identify the fluid type and levels of contamination.

DETAILED DESCRIPTION

Figure 1:
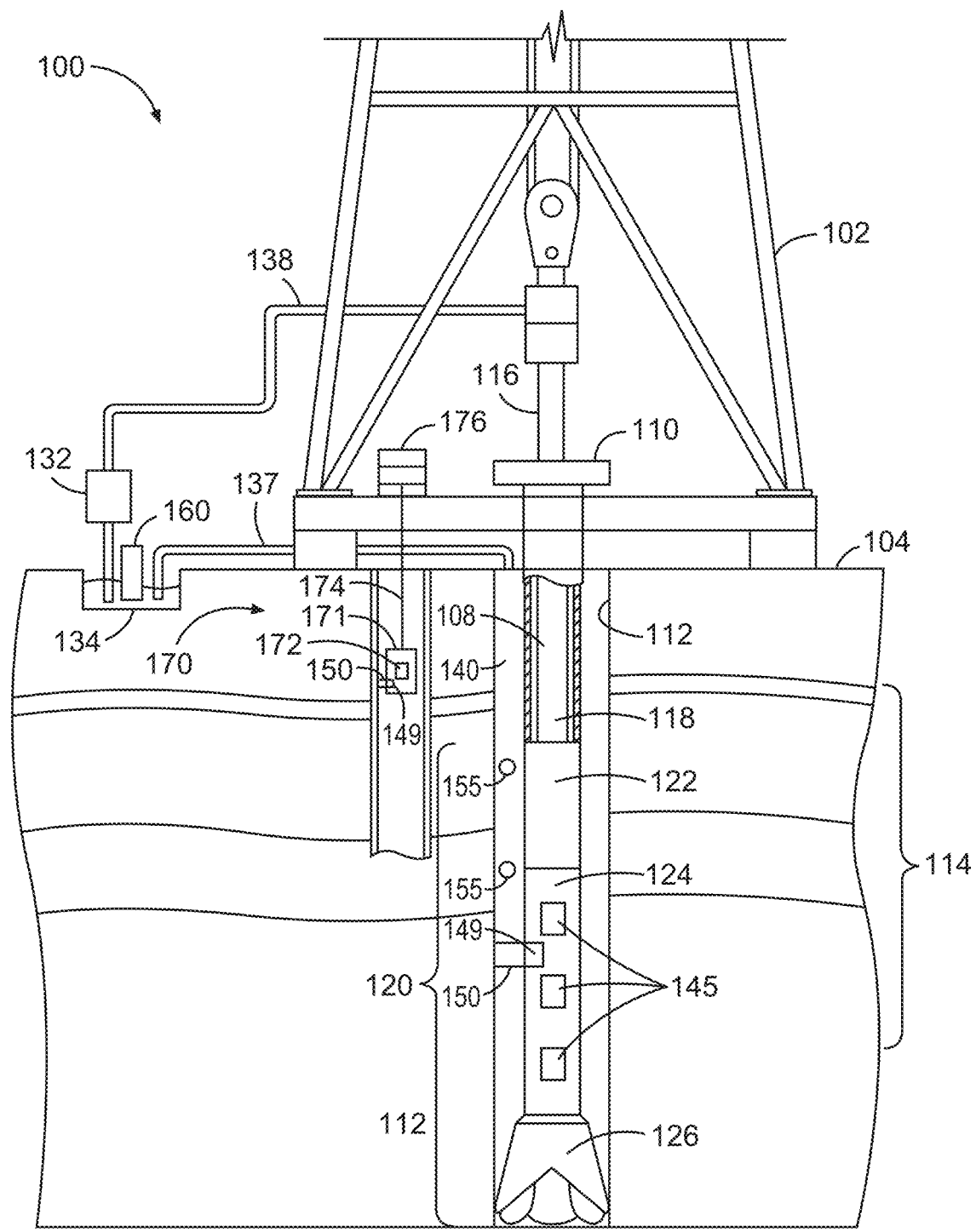
FIG. 1 illustrates a side, cut-away view of a down hole tool according to various embodiments.

In the following description of some embodiments of the present invention, reference is made to the accompanying drawings which form a part hereof, and in which are shown, by way of illustration, specific embodiments of the present invention which may be practiced. In the drawings, like numerals describe substantially similar components throughout the several views. These embodiments are described in sufficient detail to enable those skilled in the art to practice the present invention. Other embodiments may be utilized and structural, logical, and electrical changes may be made without departing from the scope of the present invention. The following detailed description is not to be taken in a limiting sense, and the scope of the present invention is defined only by the appended claims, along with the full scope of equivalents to which such claims are entitled.

A method and apparatus is provided herein that allows for fluid types to be identified with greater accuracy, for example during the sampling process. During drilling or formation testing operations, the formation fluid is tested to determine the presence of certain fluids. During collection of fluid samples, the fluid can be homogenous and/or heterogeneous, and granular flow properties may also exist.

The embodiments herein utilize the effects of segregation to improve the accuracy of fluid property measurements. The embodiments include identifying fluid changes that vary over a parameter such as, but not limited to, time, fluid sensor measurement, piston position, or volume, and analyze when the fluid changes occur, based on the parameter, and data can be obtained as to the fluid type, and/or contamination of the fluid as a function of the parameter. Using this analysis, the system can predict the occurrence of a fluid type such as gas, oil, water, or contaminate. A sample chamber valve can be selectively opened and closed to accept the desired fluid into a sample chamber.

FIGS. 1-4 illustrate systems and portions of the system for implementing the embodiments. FIG. 1 illustrates an option for a system 100 for drilling operations, in accordance with embodiments of the invention. It should be noted that the system 100 can also include a system for pumping operations, or other operations. The system 100 includes a down hole tool 124 that is associated with a drilling rig 102 located at a surface 104 of a well. The drilling rig 102 provides support for the down hole tool, including a drill string 108. The drill string 108 penetrates a rotary table 110 for drilling a borehole 112 through subsurface formations 114. The drill string 108 includes a Kelly 116 (in the upper portion), a drill pipe 118 and a bottom hole assembly 120 (located at the lower portion of the drill pipe 118). The bottom hole assembly 120 may include drill collars 122, a down hole tool 124 and a drill bit 126. The down hole tool 124 may be any of a number of different types of tools including measurement-while-drilling (MWD) tools, logging-while-drilling (LWD) tools, etc.

During drilling operations, the drill string 108 (including the Kelly 116, the drill pipe 118 and the bottom hole assembly 120) may be rotated by the rotary table 110. In addition or alternative to such rotation, the bottom hole assembly 120 may also be rotated by a motor that is down hole. The drill collars 122 may be used to add weight to the drill bit 126. The drill collars 122 also optionally stiffen the bottom hole assembly 120 allowing the bottom hole assembly 120 to transfer the weight to the drill bit 126. The weight provided by the drill collars 122 also assists the drill bit 126 in the penetration of the surface 104 and the subsurface formations 114.

During drilling operations, a mud pump 132 optionally pumps drilling fluid, for example, drilling mud, from a mud pit 134 through a hose 136 into the drill pipe 118 down to the drill bit 126. The drilling fluid can flow out from the drill bit 126 and return back to the surface through an annular area 140 between the drill pipe 118 and the sides of the borehole 112. The drilling fluid may then be returned to the mud pit 134, for example via pipe 137, and the fluid is filtered. The drilling fluid cools the drill bit 126 as well as provides for lubrication of the drill bit 126 during the drilling operation. Additionally, the drilling fluid removes the cuttings of the subsurface formations 114 created by the drill bit 126.

The down hole tool 124 may include one to a number of different sensors 145, which monitor different down hole parameters and generate data that is stored within one or more different storage mediums, for example, within the down hole tool 124. The type of down hole tool 124 and/or the type of sensors 145 thereon may be dependent on the type of down hole parameters being measured. Such parameters may include density, resistivity, capacitance, dielectric properties, acoustic properties, Nuclear Magnetic Resonance (NMR) properties, bubble point, temperature, optical, chemical, component or combinations thereof. The sensors are configured to periodically measure a down hole fluid property of a parameter, such as, but not limited to, time, volume, pump piston position, or valve status (open or closed). A processor is further optionally included and is operable to group fluid measurements in one or more categories, each category having fluid measurements falling within a range. The processor is operable to group the fluid measurements as a function of the parameter, and to identify a fluid type based on the grouping of fluid measurements.

The down hole tool 124 further includes a power source 149, such as a battery or generator. A generator could be powered either hydraulically or by the rotary power of the drill string. The down hole tool 124 includes a formation testing tool 150, which can be powered by power source 149. In an embodiment, the formation testing tool 150 is mounted on a drill collar 122. The formation testing tool 150 engages the wall of the borehole 112 and extracts a sample of the fluid in the adjacent formation via a flow line.

FIG. 1 further illustrates an embodiment of a wireline system 170 that includes a down hole tool 171 coupled to a base 176 by a logging cable 174. The logging cable 174 may include, but is not limited to, a wireline (multiple power and communication lines), a mono-cable (a single conductor), and a slick-line (no conductors for power or communications). The base 176 is positioned above ground and optionally includes support devices, communication devices, and computing devices. The tool 171 houses a formation testing tool 150 that acquires samples from the formation. In an embodiment, the power source 149 is positioned in the tool 171 to provide power to the formation testing tool 150. The tool 171 may further include additional testing equipment 172, such as the sensors and/or processor as discussed above. The sensors can be configured to periodically measure a down hole fluid property over a parameter, as discussed further below. In operation, a wireline system 170 is typically sent down hole after the completion of a portion of the drilling. More specifically, the drill string 108 creates a borehole 112. The drill string is optionally removed and the wireline system 170 is inserted into the borehole 112 for testing the formation fluid. Alternatively a logging while drilling system can be designed with similar capabilities to a wireline tool and does not require the drill string to be removed before sampling.

Figure 2:
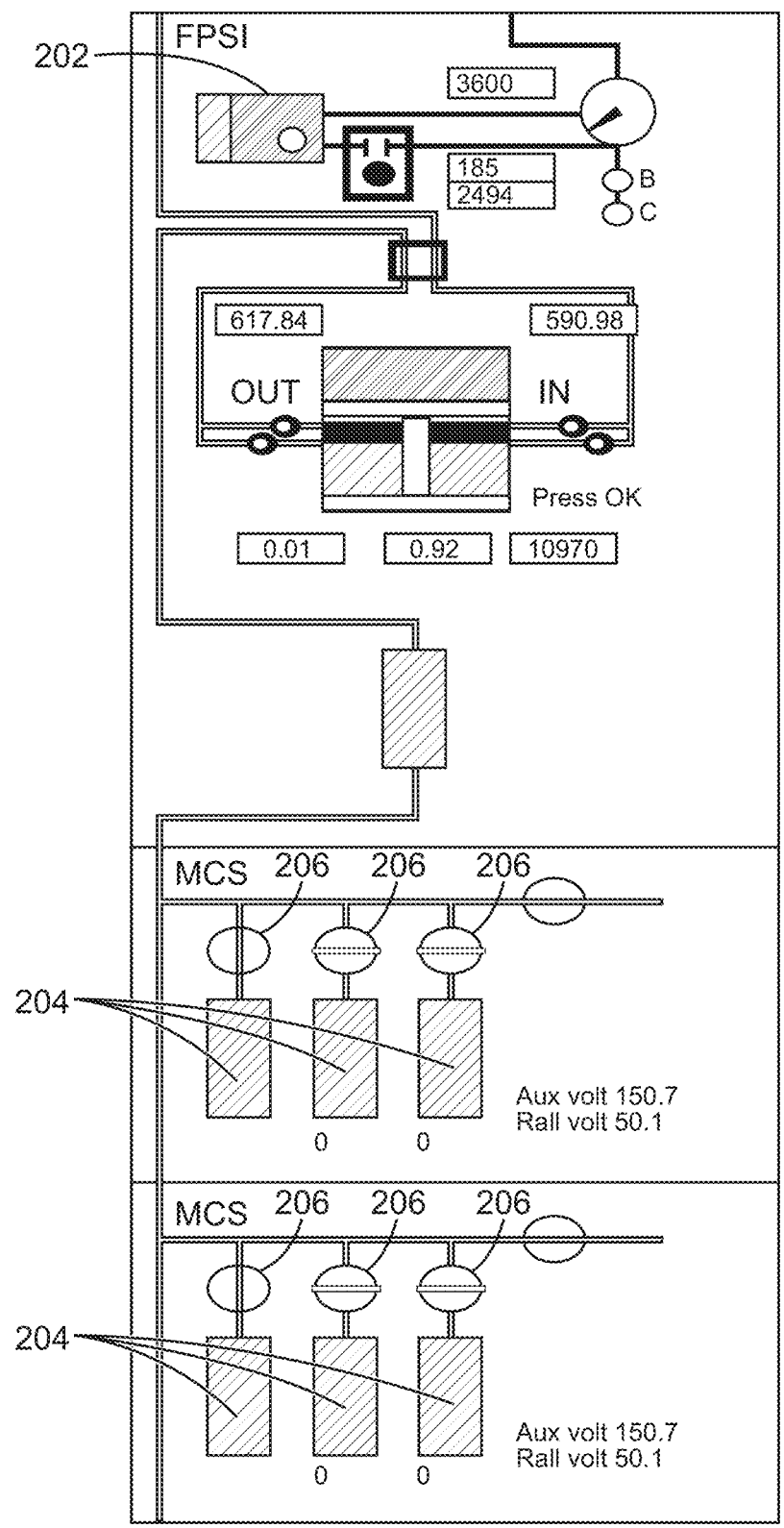
FIG. 2 illustrates a block diagram of a system according to various embodiments.

FIG. 2 illustrates a block diagram including a pump 202, and a sensor, such as a density sensor, at the outlet of the pump 202. In an option, one or more sample chambers 204 are included so that selective samples of the fluid can be taken. Sample chamber valves 206 can be selectively opened during the cycle of the pump to retrieve a fluid sample during a selected phase of the pump stroke. For instance, once the methodology is used to correlate when a certain fluid type can be found at a certain value of a parameter, such as at a certain time, volume, or pump stroke position, the sample chamber valves 206 can be opened at the value where the desired fluid type can be sampled. In a further option, multiple valves 206 and multiple sample chambers 204 can be incorporated so that different samples can be taken at different fluid phases. For instance, a first sample chamber can sample water, and a second sample chamber can sample oil. In another option, another sample chamber can sample gas. In yet another option, the sample chambers can be used to extract contaminated fluid. In yet another option, the valves 206 can be used to exclude a particular fluid type.

Figure 3:
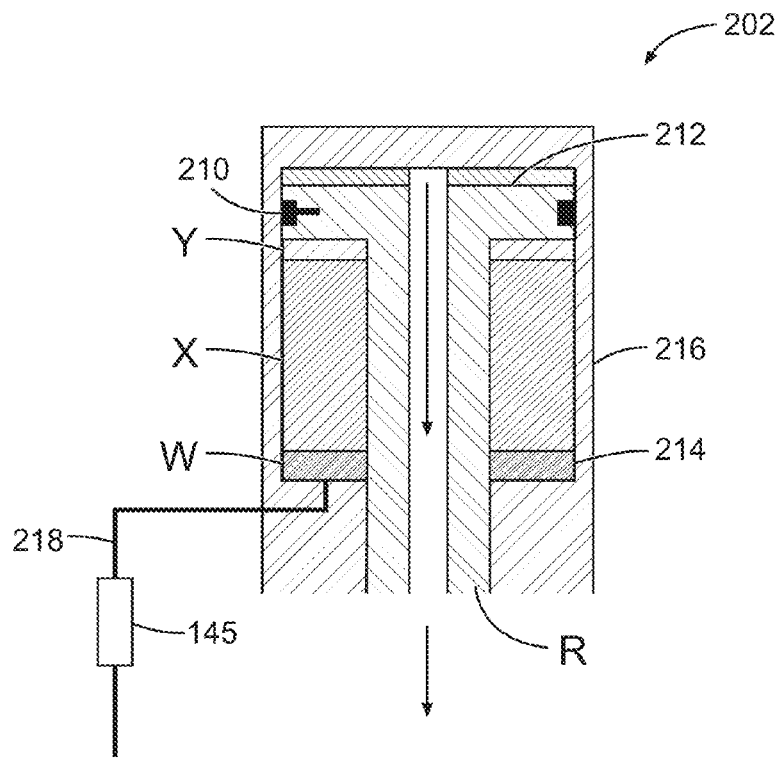
FIG. 3 illustrates a cross-sectional view of a portion of the down hole tool according various embodiments.

FIG. 3 illustrates an example of a device that can be used to displace fluid either from the well bore from the chamber 216, such as a pump 202, which can assist in segregating the fluid. Other types of devices or methods can be used to segregate the formation fluid. For instance, the formation fluid can segregate naturally or induced by gravitational, or centrifugal forces or electrical potential. Other fluid properties such as viscosity, capillary pressure, immiscibility and electrical conduction effects can also cause fluids to separate.

The pump 202 includes a piston 210 which moves from a position a 0%, 212, to a position at 100%, 214. As the piston 210 moves within the chamber 216 of the pump 202, the piston 210 displaces fluid from the chamber 216 through the flow line 218, where the flow line 218 has a smaller diameter than the chamber 216.

A sensor 145 can be disposed along the flow line 218, allowing for one or more properties of the formation fluid to be measured as the piston 210 displaces fluid from the chamber 216. For example, the sensor can measure density, resistivity, capacitance, dielectric properties, acoustic properties, NMR properties, bubble point, temperature, optical properties, or combinations thereof. In an option, as the sensor measures the fluid property, a parameter such as piston position can be detected and noted so that fluid properties are taken at different values of the parameter (i.e. the piston position). The piston position is merely one option of a parameter, however, other parameters such as, but not limited to, volume, time, fluid sensor measurement can be used.

In an example, the sensor can measure a density of the fluid at various positions of the piston 212. The changes in the density measurements can be separated and grouped in to measurement bins. The measure bins, in an option, are defined by a range of density indicating a fluid type. The bins allow for analysis and categorization of the fluid types as a function of a parameter, such as piston stroke position.

Figure 4:
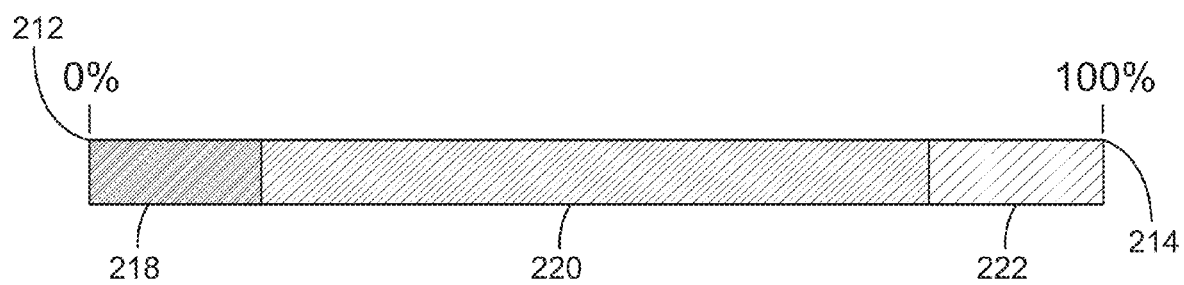
FIG. 4 illustrates a portion of the down hole tool according various embodiments.
Figure 5:
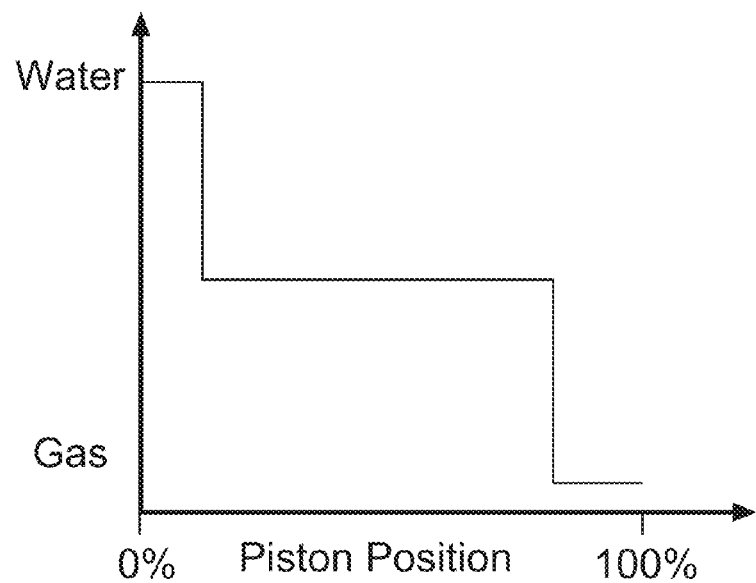
FIG. 5 illustrates a graph illustrating data measurements over a parameter according to various embodiments.

The fluid type changes over the changing parameter (i.e. piston stroke position), as shown for example in FIGS. 4 and 5. In FIG. 4 it can be seen that the fluid discharged begins as a first fluid type 218 having a density falling within a first range, changing to a second fluid type 220 having a density falling within a second range, and further changing to a third fluid type 222 having a density falling within a third range, depending on the stroke position of the piston. FIG. 5 illustrates the transition of the fluid from water to gas as the piston stroke position moves from 0% to 100%.

Figure 6:
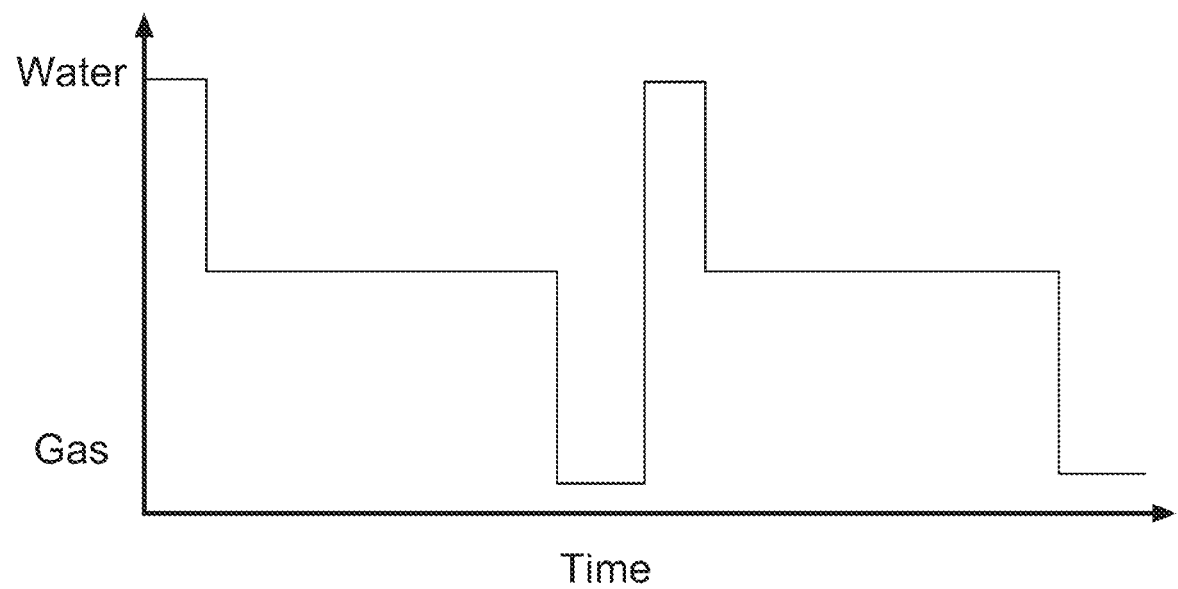
FIG. 6 illustrates a graph illustrating data measurements over a parameter according to various embodiments.

The sensor measurements can be plotted and correlated with one or more parameters, such as piston stroke position, as shown in FIG. 5, or another parameter, such as time. FIG. 6 illustrates the measurements made of the formation fluid as a function of time. FIG. 6 further illustrates the cyclical nature of the density measurements, and resulting fluid identification over a parameter, such as time. This method may use the cyclical nature of the measurement to determine a fluid cycle over time, and may also calculate or correct the position of the piston as it relates to actual movement of fluids, variation of the slip velocity, or compressibility of the fluid(s).

Figure 7:
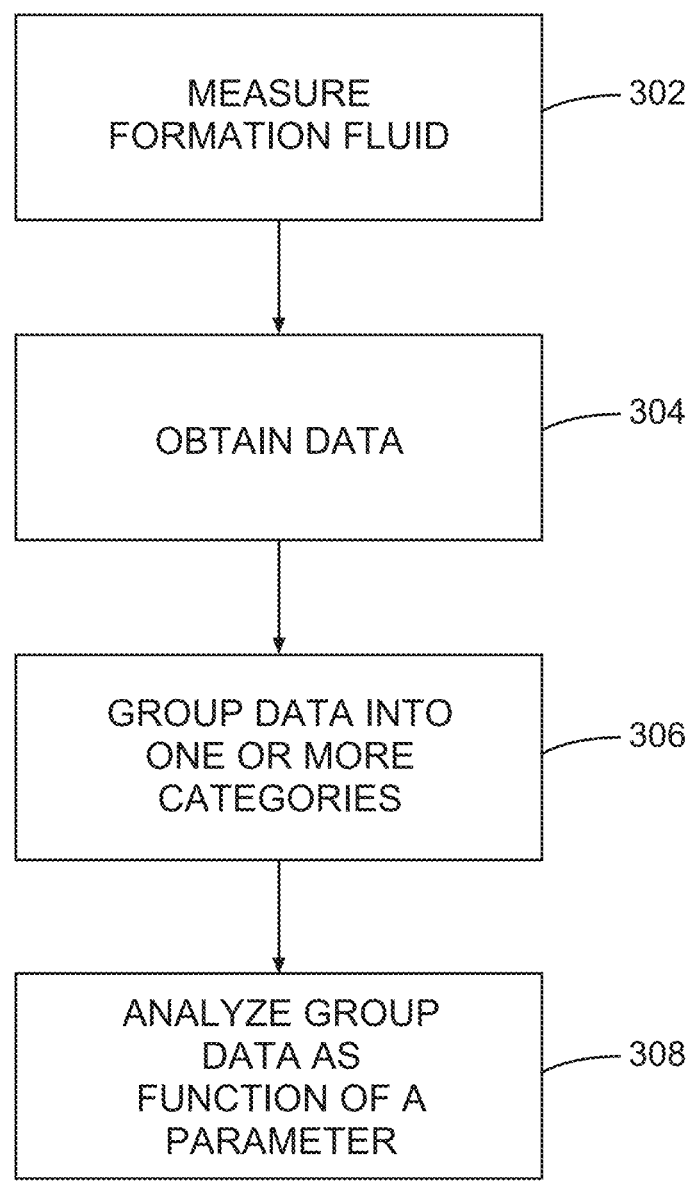
FIG. 7 illustrates a method flow diagram according to various embodiments.

A method for determining fluid types with a system is further described. Referring to FIG. 7, the method includes measuring, for instance, formation fluid 302 or a fluid property of formation fluid in a borehole with a down hole tool and obtaining data 304, where the data has measurement levels that vary over a parameter. Examples of parameters include, but are not limited to, time, volume expelled from a chamber, piston stroke position, sensor measurements, or combinations thereof. Measuring the formation fluid optionally includes measuring for one or more of density, resistivity, capacitance, dielectric properties, acoustic properties, NMR properties, bubble point, temperature, optical, chemical, or compositional properties.

The method further includes grouping data in one or more categories 306, where each category has data falling within a range. Optionally, the method further includes manipulating the fluid, such as pumping the fluid, or segregating the fluid, for instance while measuring the fluid.

Further included in the method is analyzing the grouped data as a function of the parameter 308. Analyzing the grouped data optionally includes identifying at least one fluid type of the formation fluid using the grouped data, and/or characterizing a heterogeneity of the formation fluid. In another option, analysis the grouped data optionally includes analyzing the grouped data as a function of time, amplitude, i.e. amplitude of the piston stroke position, or volume, or combinations thereof. Further options for the method include selectively sampling the fluid, or selectively excluded. For instance, the fluid is sampled or excluded after the grouped data is identified as a particular fluid type. In another option, the method can be used to estimate contamination of the sample.

Figure 28:
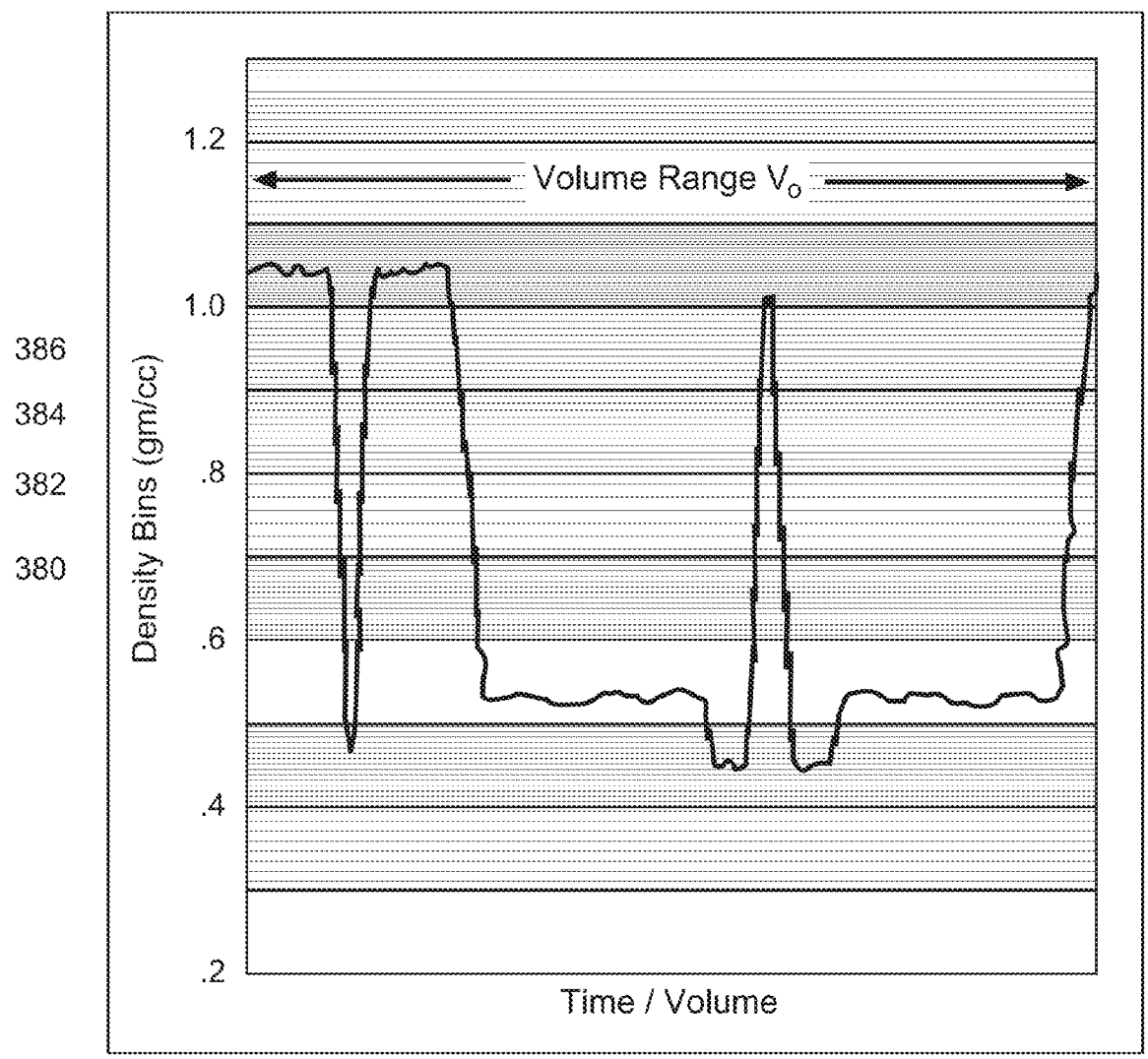
FIG. 28 illustrates a graph illustrating data measurements over a parameter according to various embodiments.

An example of density sensor measurements is shown in FIG. 28. Assuming the in-situ oil density is less than water, the water filtrate is detected with the high density measurements $\rho_{max}$ and the oil (or gas) with the lower measurements, $\rho_{min}$. The base-line averaged curve is an estimate of the fluid mixture $\rho_{mix}$. By making the assumption that these early measurements actually detect the water filtrate and the native formation fluids, it is possible to make an estimate of the fluid contamination C as follows:

$$C = \frac{\rho_{mix} - \rho_{min}}{\rho_{max} - \rho_{min}}(\%)$$

This contamination estimate also assumes the mixing model is linear with density. Now assuming the standard deviations of the measurements are known, an additive error analysis is used to estimate the standard error of contamination.

$$S_c = C\sqrt{\frac{\sigma_{mix}^2 + \sigma_{min}^2}{(\rho_{mix} - \rho_{min})^2} + \frac{\sigma_{max}^2 + \sigma_{min}^2}{(\rho_{max} - \rho_{min})^2}}$$

Using the density sensor resolution of 0.003 gm/cc as the standard error for the measurements, a standard error of 1.4% is determined from the above equation for a typical WBM and oil sample (i.e., $\rho_{max}$=1.0, $\rho_{min}$=0.7) at low levels of contamination. A similar contamination analysis can be made using the resistivity or types of fluid sensor responses.

Figure 8:
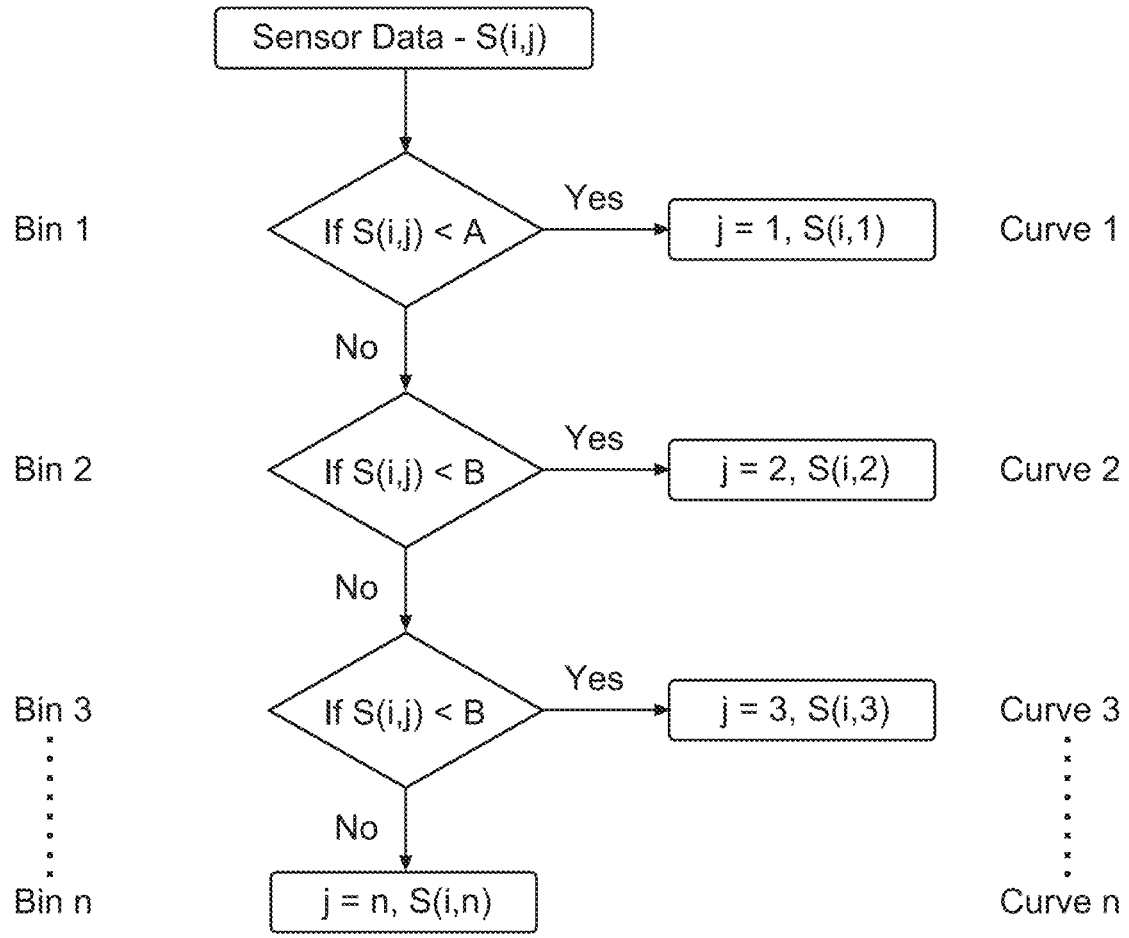
FIG. 8 illustrates a method flow diagram according to various embodiments.

Further details for the method as are follows. In a system as described above, a series of measurement values S can be taken over a parameter, such as time, and each reading in the series has a unique index, i. The series of measurement values can be grouped or binned into unique curves using several techniques. In an option, a technique involves grouping the bins into different reading levels as shown in FIG. 8. In this logic diagram, three levels are shown (i.e., A, B, C) but the method is not necessarily limited to three, and can include additional levels. In an option, A represents the cutoff measurement or a range for a first fluid type, such as gas, so that a sensor measurement less than A would be given a unique bin identifier of j=1 to be plotted as a unique Curve 1 representing the sensor gas readings. If the sensor reading is in the range between A and B, it could be classified as a second fluid type, such as an oil, and given a unique bin identifier of j=2 and plotted as Curve 2. If the last bin represented the cutoff or range for a third fluid type, such as water, then any reading greater than C would have j=3 and plotted as Curve 3. Additional ranges are possible to identify additional fluid types. Each curve can have a unique visual identifier for each fluid type. For example, each curve can have a different color to show the fluid type (i.e., red, green, blue for gas, oil and water respectively).

In another option for the method, a method for sampling formation fluid includes introducing formation fluid into a pump, the pump having an inlet and an outlet. The method further includes segregating the fluid within the pump, pumping fluid out through a flowline, and sensing fluid with a fluid sensor and obtaining sensor data, where sensing fluid includes sensing fluid with the fluid sensor at or downstream of the outlet of the pump. The method further includes selectively opening and closing a valve and accepting a desired fluid in at least one sample chamber based on the sensor data, where the valve is open and closed while the fluid is pumped out through the flowline.

Various options for the method are as follows. For instance, the method is optionally performed until at least one sample chamber is filled. In another option, the method includes filling one sample chamber with one fluid type and additional sample chambers are filled with at least one other fluid type. In another option, sensing fluid with the fluid sensor includes sensing density of the fluid, resistivity, capacitance, dielectric properties, acoustic properties, NMR properties, bubble point, temperature, optical, chemical, compositional or combinations thereof. The method can also be used in conjunction with the grouping or binning techniques described herein.

Figure 9:
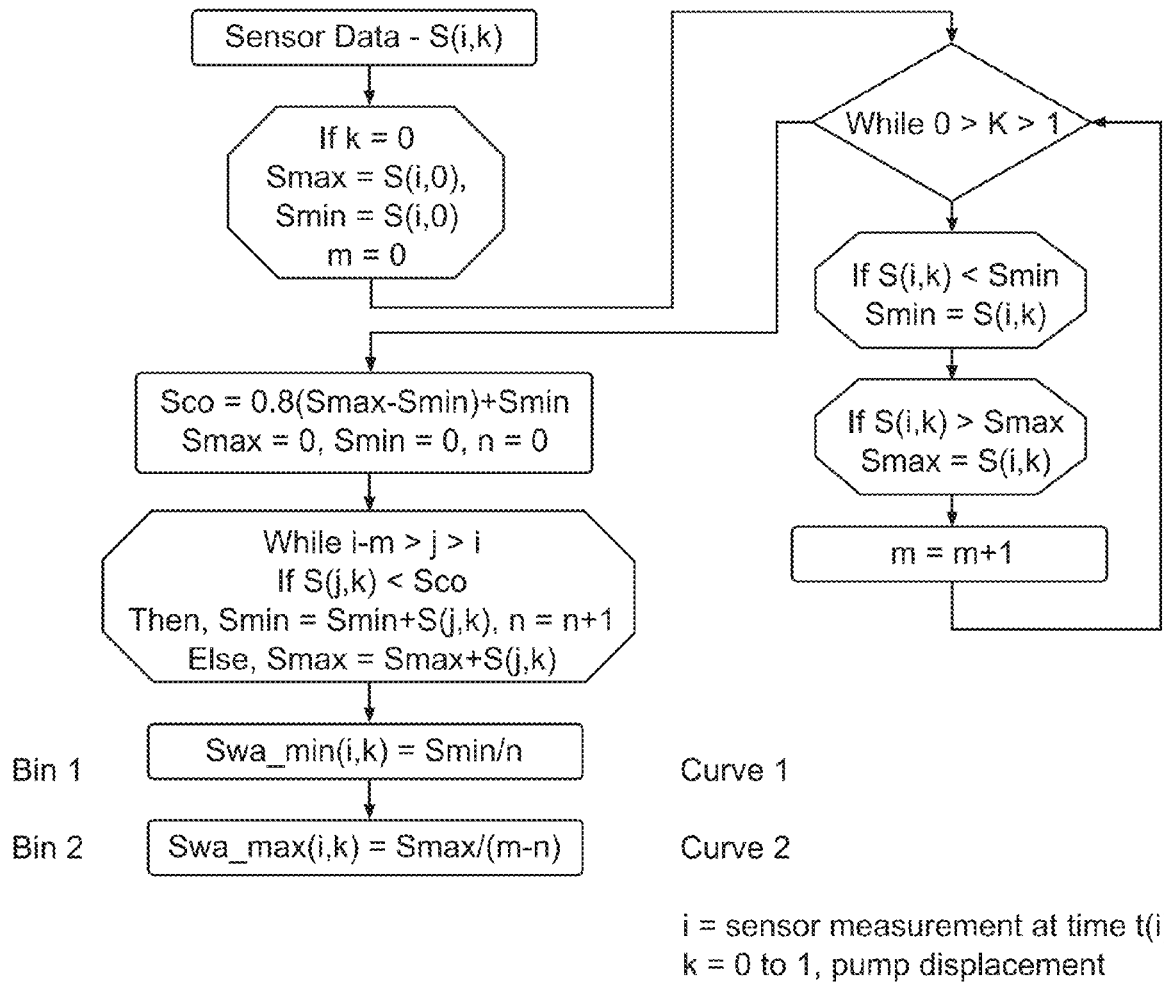
FIG. 9 illustrates a method flow diagram according to various embodiments.

Referring to FIG. 9, the data can be further processed or analyzed to determine the fractional quantities of the bins. For example, consider a series of measurements where m is the number of measurements made. The number of measurements could be based on a parameter such as a time interval, volume expelled, or some logical event in the testing tool like the stroke of a pump, or a fraction of the pump stroke. Using m measurements, the fractional flow of fluid types can be determined as follows.

$$\text{Type 1, Gas Fraction} = \frac{\sum_{i}^{i+m} \text{for } (i, j) \text{ if } (j = 1, 1, 0)}{m}$$

$$\text{Type 2, Oil Fraction} = \frac{\sum_{i}^{i+m} \text{for } (i, j) \text{ if } (j = 2, 1, 0)}{m}$$

$$\text{Type 3, Water Fraction} = \frac{\sum_{i}^{i+m} \text{for } (i, j) \text{ if } (j = 3, 1, 0)}{m}$$

$$\text{Type } n, \text{Fraction} = \frac{\sum_{i}^{i+m} \text{for } (i, j) \text{ if } (j = n, 1, 0)}{m}$$

These quantities can be plotted on a curve from 0 to 1 showing the fluid fraction changes over a parameter, such as time. This is an alternative way of plotting the data that can supplement plotting the binned curves 1, 2, 3 . . . n. In another option, the data can be grouped using the relative velocities of the fluid fractions. In this case, the changes in the fluid fractions are tracked within the m measurements. By knowing the total fluid velocity, the relative velocities of each fluid fraction can be determined and plotted.

Using the type of grouping or binning shown in FIG. 8 applied over a reoccurring event such as a pump stroke, a new type of processing can be applied to produce weighted average curves. This is illustrated in FIG. 9, where k represents a reoccurring event such as the pump piston position over the pump cycle. For example, k could be a fraction from 0 to 1 where 0 represents the pump piston in its uppermost position and 1 in its lowest position. During a pump cycle, there is a maximum and minimum value recorded during this period (i.e., $S_{max}$, $S_{min}$). From these maxima and minima, a sensor cutoff, $S_{co}$, can be established such as some fraction between the $S_{max}$ and $S_{min}$ values. Two categories or bins can be established similar to the logic of FIG. 8, where the values above and below the sensor cutoff, $S_{co}$, are stored. The stored values can be averaged creating two curves where one is the weighted average above the $S_{co}$ and the other below.

In another option, the method of binning or grouping the data by a parameter including tool events, such as fractions of the pump displacement. In this case, where k represents fractions of a pump stroke, data that is recorded during fractional displacement of the pump can be recorded in bins and plotted as separate curves (i.e., k=¼, ½, ¾, 1). The fractional periods do not necessarily need to be evenly spaced. Also, other parameters including tool events can be used, such as the duration of a valve opening or closing.

Figure 10:
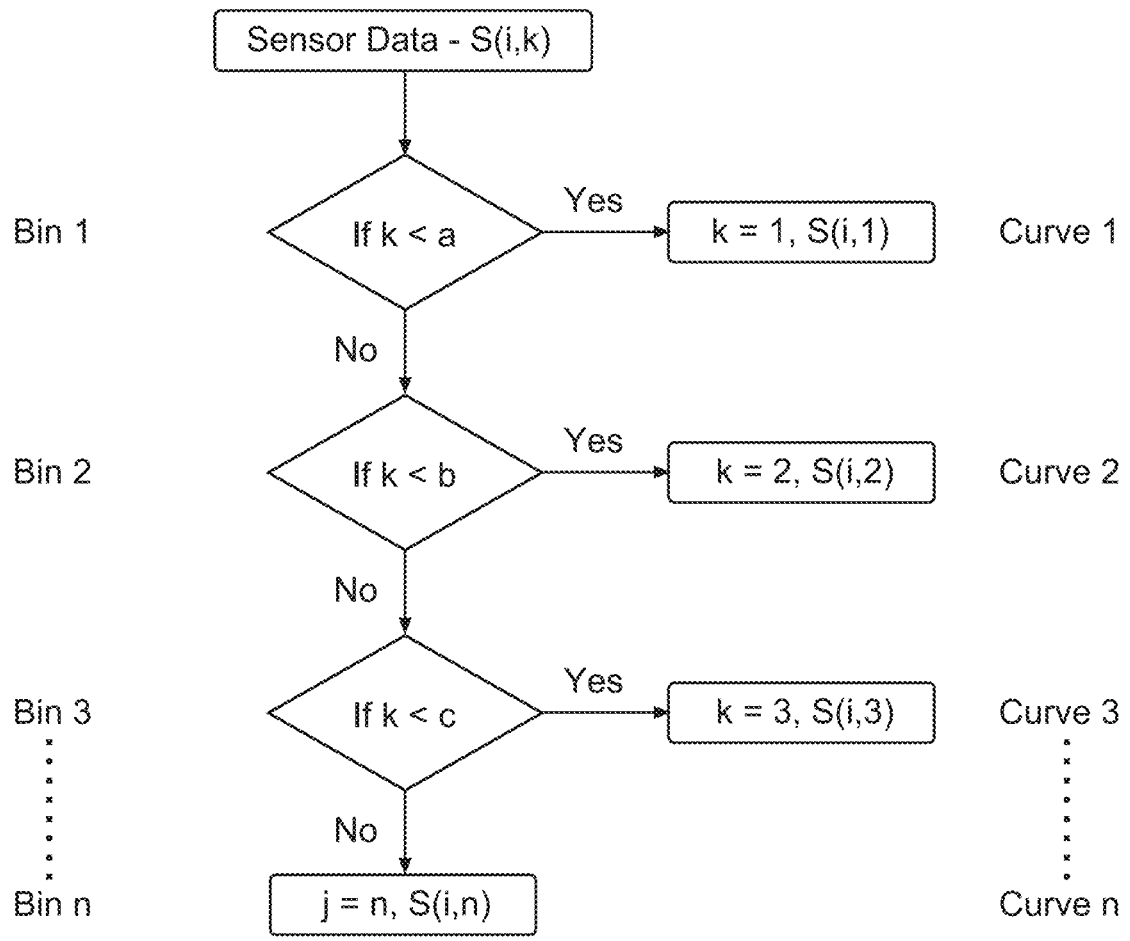
FIG. 10 illustrates a method flow diagram according to various embodiments.

FIG. 10 illustrates a method for grouping data such as the sensor measurements into categories or bins that are related to a parameter such as the pump piston position. Because the pump or other reoccurring events in the tool can tend to separate fluids, the binned curves defined by this logic provide a method of observing fluid mixture changes over time and help to determine when to take a representative sample of fluid.

Figure 11:
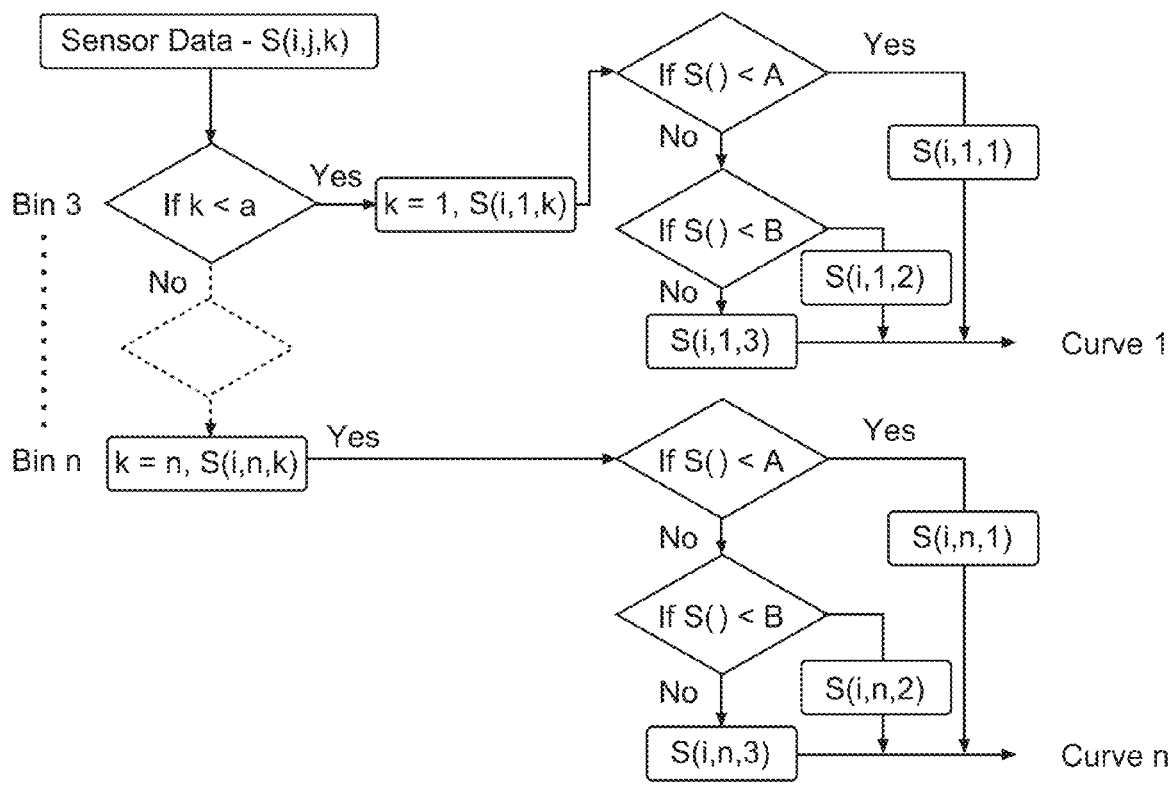
FIG. 11 illustrates a method flow diagram according to various embodiments.

The data obtained via the sensor measurements can be further analyzed as shown in FIG. 11, which enhances the logic shown in FIG. 10, where within each fractional value of parameter k (i.e., pump position) the type of fluid can be identified using the sensor level cutoff method shown in FIG. 8. Within the bins or categories, the test for fluid type is made so that a new attribute can be added, such as color, based on the fluid type.

The initial logic steps in FIG. 11 could be based on the sensor cutoff as shown in FIG. 8. The categories or bins can be further analyzed with an additional logic step as shown in FIG. 11. For example, as an additional step, the data could be averaged over incremental time periods in each bin to create smoothed binned curves. Further logic steps can be added depending on the sensor data providing the best indication of fluid changes in the system over a parameter such as time or events.

FIGS. 24-29 relate to another apparatus and method for measuring fluid properties. Fluid sensors tend to provide erratic results when sampling multiphase fluids. These conditions are encountered when sampling oil in the presence of water-based mud, water in oil-based mud and gas in either water-based mud or oil-based mud.

Figures 24, 25, 26:
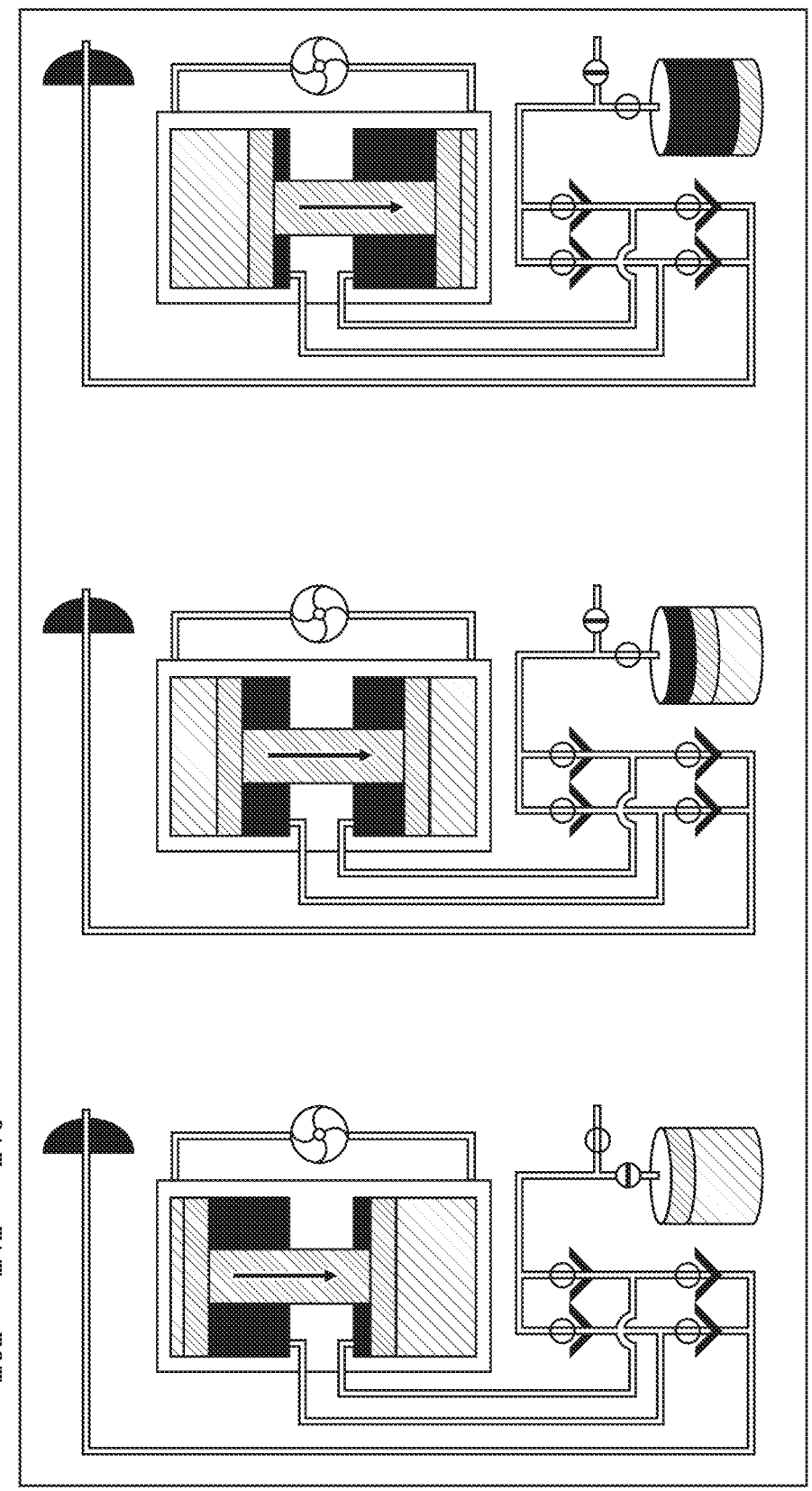
FIG. 24 illustrates a block diagram of a system according to various embodiments.
FIG. 25 illustrates a block diagram of a system according to various embodiments.
FIG. 26 illustrates a block diagram of a system according to various embodiments.

FIGS. 24-26 illustrate a pump 202 with a piston 212 within a chamber 216. The pump 202, in an option, is a double-acting pump in which a dog-bone style piston moves up and down. When an upper chamber 217 is filling with fluid, phases of the fluid can separate with the lighter gas at the top, then oil and water. The upper chamber 217 of the pump 202 is filled with fluid that has segregated and when the piston 202, moves down, as indicated by the arrow, water, oil and gas are expelled sequentially. For instance, as the piston 212 moves down, water is initially expelled from the lower chamber 219 through the flow lines followed by the oil and gas as the piston 212 progresses. The reverse happens when the piston 212 travels upward. A sensor is further included with the system, such as a density sensor that provides density sensor measurements taken at various parameter, such as piston stroke position.

Figure 27:
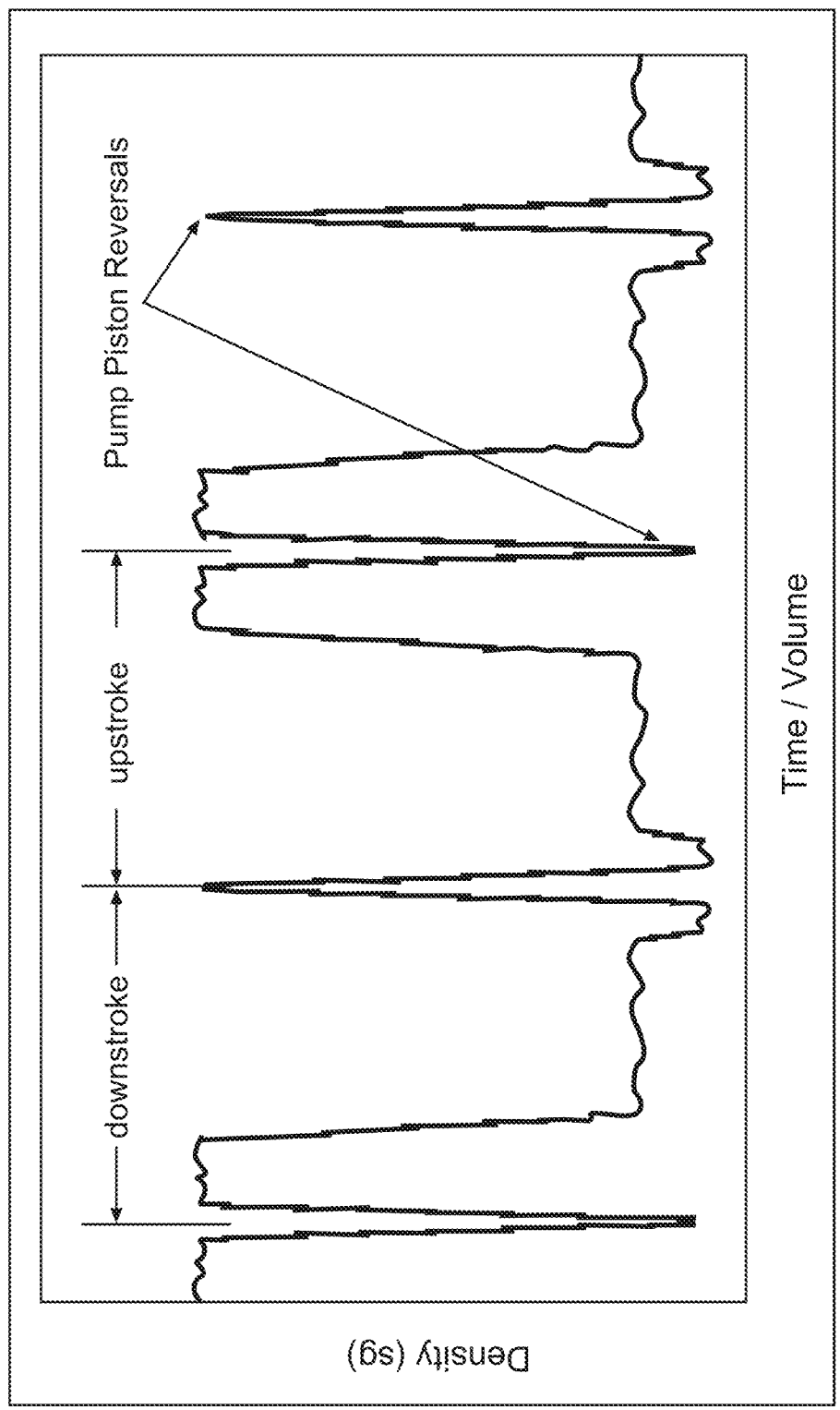
FIG. 27 illustrates a graph illustrating data measurements over a parameter according to various embodiments.

In analyzing the density sensor data relative to the parameter of piston stroke, the measurements followed the sequence of the piston movements as shown in FIG. 27, which shows changes in density that correspond to the segregated fluids and pump position as the fluids leave the pump 202. When the piston 212 changes direction, there may be some remaining residual fluid from the last stroke trapped in between the pump 202 and the check valves. When the piston 212 finishes a down or upstroke this small volume of trapped residual fluid is expelled before the fluids in the pump chamber are expelled. Since this trapped fluid is from the end of a pump stroke it will contrast in density with the fluid in the pump chamber at the beginning of the piston stroke. This contrast causes the spikes in the density curve when the pump reverses.

Fluid segregation can also be detected using the density sensor. This makes it possible to estimate the relative volumes of the fluid being pumped during each pump stroke, as illustrated in FIG. 28, where the density is divided into bins or groups that represent transitions of fluid types. A bin or group, in an option, is defined as a 0.1 gm/cc density range. In an option, industry standard colors represent the four basic fluid types. Green, represented by 380, represents a typical oil density range, red, represented by 382, represents gas, blue represented by 384, represents water, and brown, represented by 386, represents mud. Other colors are used to represent the transition from one basic fluid type to another. By adding up the number of measurements that exist within each fluid density bin and dividing by the total number of measurements made during a pump stroke, a map of the fluid distribution can be made. This process can be repeated for successive pump strokes and a time log constructed showing the progression of the fluid distribution as shown in FIG. 28. Another method of plotting this fluid distribution log is to update the fluid distribution at regular time intervals while still summing over a representative volume displaced by the pump.

Figure 29:
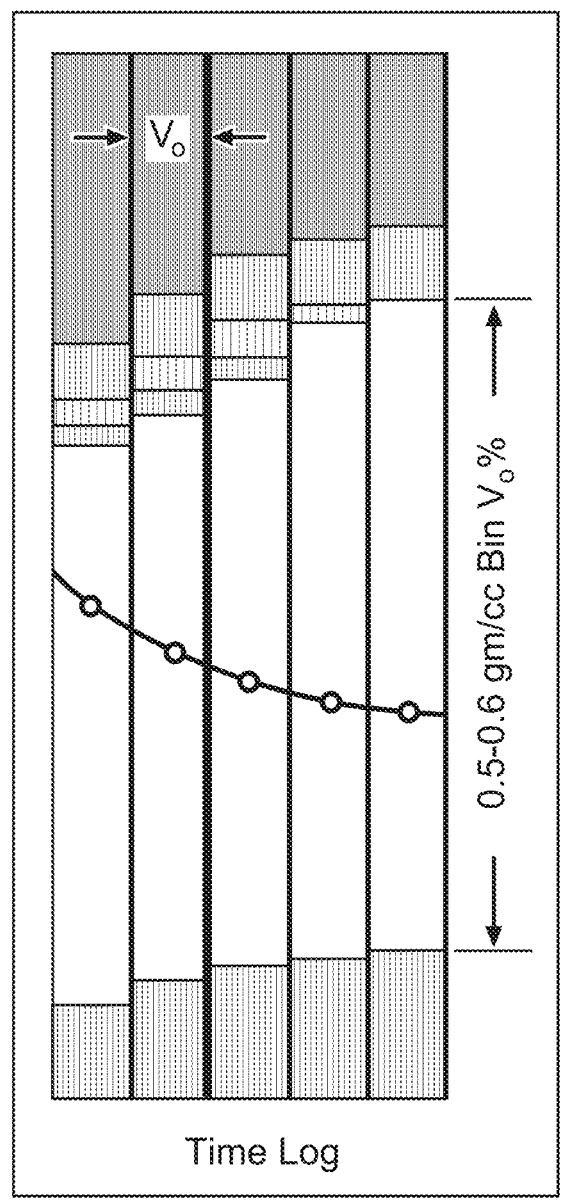
FIG. 29 illustrates a graph illustrating data measurements over a parameter according to various embodiments.

Another curve is shown on the time log in FIG. 29, which is the average of all the density values over the same representative volume. This base-line density curve is a method of averaging that correlates with the fluid distribution map. The base-line density curve shown in FIG. 29 is plotted over the fluid distribution map. As shown, this curve responds to fluid concentration changes and is therefore an indicator of sample cleanup. This averaged curve can be used to estimate the contamination using a trend analysis whereby a regression is used to match the density curve to a function representing cleanup and the contamination is estimated by how close the curve is approaching its asymptote. Density-based contamination compares favorably to other sensor measurements such as NMR T1, capacitance, and resistivity sensors using this trend analysis approach.

When pumping starts, mud filtrate contaminant enters the flowline. During this period of single-phase flow, the density response is consistent and variations are minor. As pumping continues, and an immiscible fluid arrives in the flowline, the pump starts to segregate the fluids and the sensors start to show the variation in the fluid properties. This behavior normally occurs with immiscible fluid mixtures encountered when sampling oil in the presence of water-based mud as well as water sampling with oil-based mud. While the pump induces fluid segregation and associated immiscible density response pattern depicted in FIG. 27, a similar behavior is observed by a resistivity sensor positioned on the inlet side of the pump near the probe. This seemingly erratic resistivity sensor behavior was previously dismissed as an unreliable sensor measurement. When a processing method described earlier for the density sensor is applied, there is a surprising trend correlation over the duration of the pump-out. Both sensors show similar fluid distribution maps and transitions from contamination to a clean sample, where log examples can be used to demonstrate this.

It should be noted that the methods described herein can be executed in iterative, serial, or parallel fashion. Information, including parameters, commands, operands, and other data, can be sent and received, and perhaps stored using a variety of media, tangible and intangible, including one or more carrier waves.

Upon reading and comprehending the content of this disclosure, one of ordinary skill in the art will understand the manner in which a software program can be launched from a computer-readable medium in a computer-based system to execute the functions defined in the software program. One of ordinary skill in the art will further understand that various programming languages may be employed to create one or more software programs designed to implement and perform the methods disclosed herein. The programs may be structured in an object-orientated format using an object-oriented language such as Java or C++. Alternatively, the programs can be structured in a procedure-orientated format using a procedural language, such as assembly, FORTRAN or C. The software components may communicate using any of a number of mechanisms well known to those skilled in the art, such as application program interfaces or interprocess communication techniques, including remote procedure calls. The teachings of various embodiments are not limited to any particular programming language or environment. Thus, other embodiments may be realized.

Figure 12:
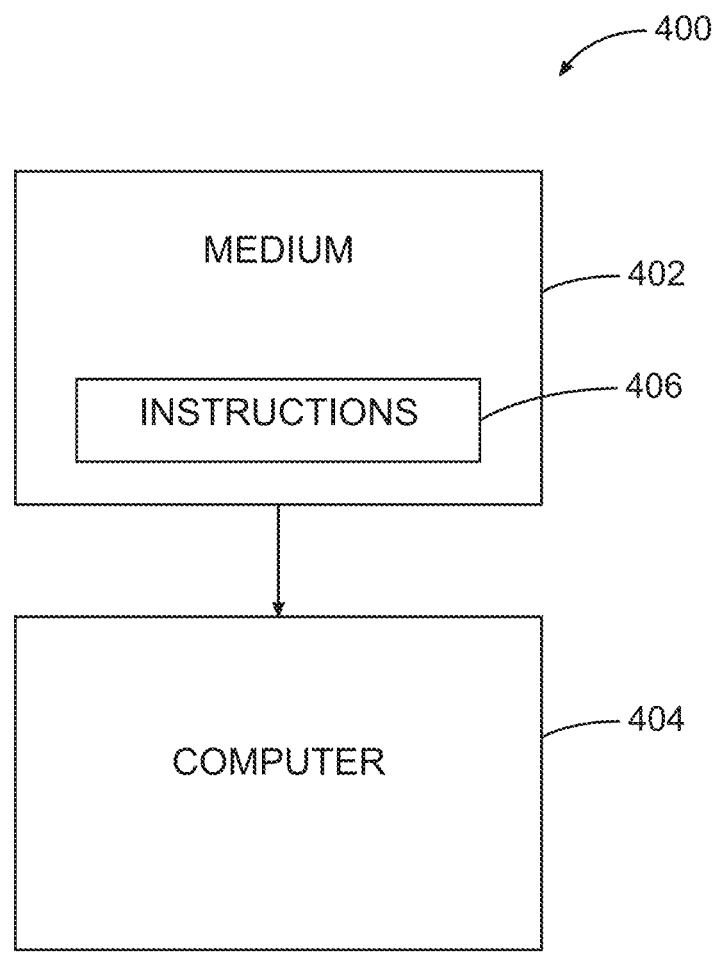
FIG. 12 illustrates a block diagram of an article according to various embodiments.

FIG. 12 is a block diagram of an article 400 according to various embodiments of the invention. The article 400 comprises an article of manufacture, such as a computer, a memory system, a magnetic or optical disk, some other storage device, and/or any type of electronic device or system. For example, the article 400 may include a processor 404 coupled to a computer-readable medium such as a memory 402 (e.g., fixed and removable storage media, including tangible memory having electrical, optical, or electromagnetic conductors) having associated information 406 (e.g., computer program instructions and/or data), which when executed by a computer, causes the computer (e.g., the processor 404) to perform a method including such actions as measuring formation fluid in a borehole and obtaining data, the data having measurement levels that vary over a parameter, grouping data in one or more categories, each category having data falling within a range, and analyzing the grouped data as a function of the parameter. In fact, any of the activities described with respect to the various methods above may be implemented in this manner.

Figure 13:
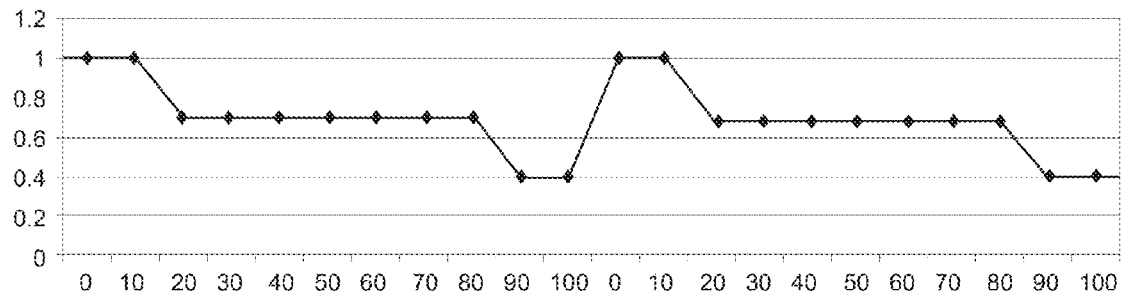
FIG. 13 illustrates a graph illustrating data measurements over a parameter according to various embodiments.
Figure 14:
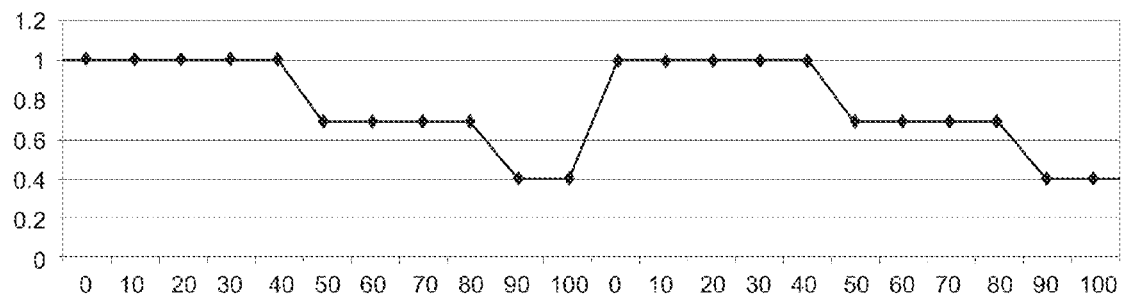
FIG. 14 illustrates a graph illustrating data measurements over a parameter according to various embodiments.

The following are examples using the various methods, systems, and down hole tools discussed above. FIG. 13 illustrates an example of density measurements plotted over two pump cycles, where the density measurements are plotted as a function of volume. For instance, the measurement can be taken at every 100 cc of fluid ejected, for a cycle that ejects 1000 cc overall. In the example shown in FIG. 13, it can be seen there is 10% water (1 g/cc), 60% oil (0.7 g/cc), 10% gas (0.4 g/cc), and 20% transitional or heterogeneous fluid. FIG. 14 illustrates another example of density measurements plotted over two pump cycles. In this example, it can be seen there is 40% water (1 g/cc), 30% oil (0.7 g/cc), 10% gas (0.4 g/cc), and 20% transitional or heterogeneous fluid. The transitional fluid may occur as the fluid transitions from water to oil, and from oil to gas, where the fluid may form an emulsion or a combination of both fluids. The fluid segregation is dynamic and eventually will be all or mostly oil. However, this method allows the density variation to be correlated with a parameter, such as a pump cycle.

Referring to FIG. 15, the top portion of the graph illustrates an example of a sample having been drawn into a pump cylinder and discharged through a density sensor. The density curve varies from 1 g/cc to 0.7 g/cc, and shows the sample is 50% water and 50% oil by volume. The large variation in fluid density indicates the fluid being pumped is heterogeneous. The lower portion of the graph at 252 illustrates how the curve 250 may be referenced to the pump stroke piston position. If segregation occurs in the pump, the density variation may be correlated to the pump cycle.

The density or other types of sensor measurements can be sampled at different points referenced to the movement of fluid. The movement of fluid may be indicated by the measurement of a parameter, such as, but not limited to time, pressure, velocity, pump piston position, pump control, flow rate, valve states or a combination of these. In the example, pump piston position can be used to group data. For instance, data can be grouped at a pump piston position at 0% (260), 50% (262), 60% (264), and 100% (266). Using these groupings, the data can be analyzed to identify the fluid types as a function of the piston stroke. In this example, the bin 0% (260)=1 g/cc, 50% (262)=1 g/cc, 60% (264)=0.7 g/cc, 0% (266)=0.7 g/cc. The data can be used to identify inflection points, at the beginning and end of the bins.

Figure 15A:
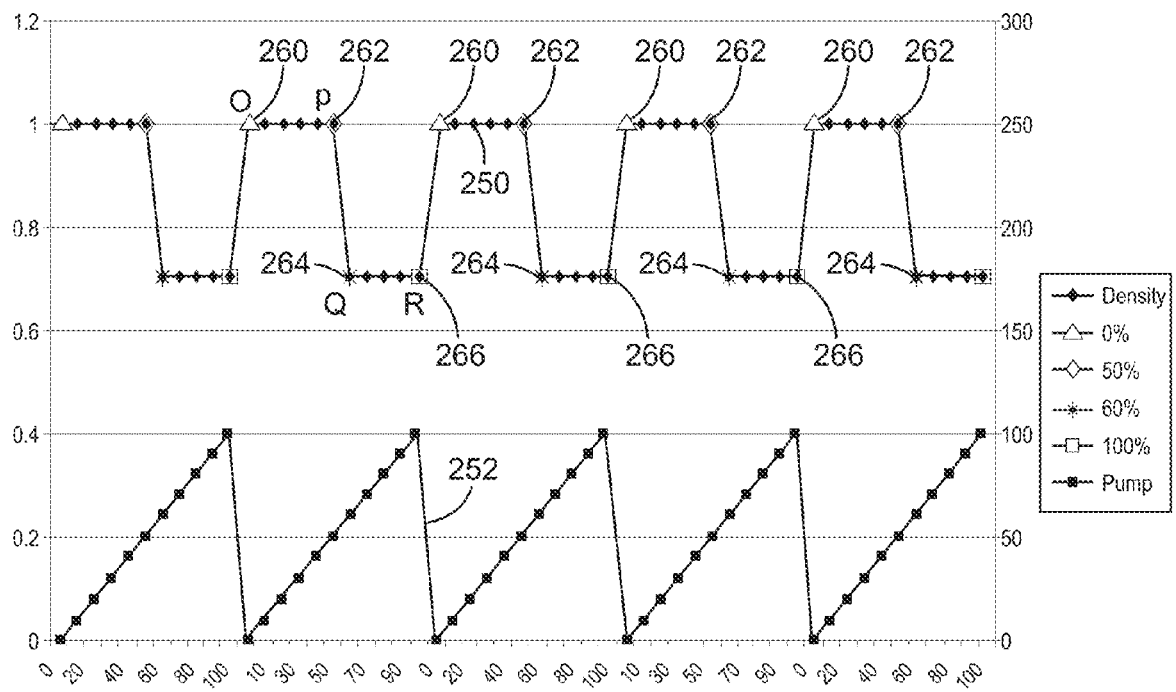
FIG. 15A illustrates a graph illustrating data measurements over a parameter according to various embodiments.

As shown in FIG. 15A, between 0 and 50% of the pump stroke, the fluid is water. As shown in FIG. 2, the valves can be opened and take a down hole fluid sample during the water phase of the pump stroke. In addition, the oil portion of the pump stroke could be placed into a separate sample bottle during the 60% to 100% of the pump stroke. The timing and mechanism of the sample collection may be affected by volume of the flow line, compressibility of the fluid, timing of the individual valves, system delays, which can be compensated for during the sample process.

Figure 15B:
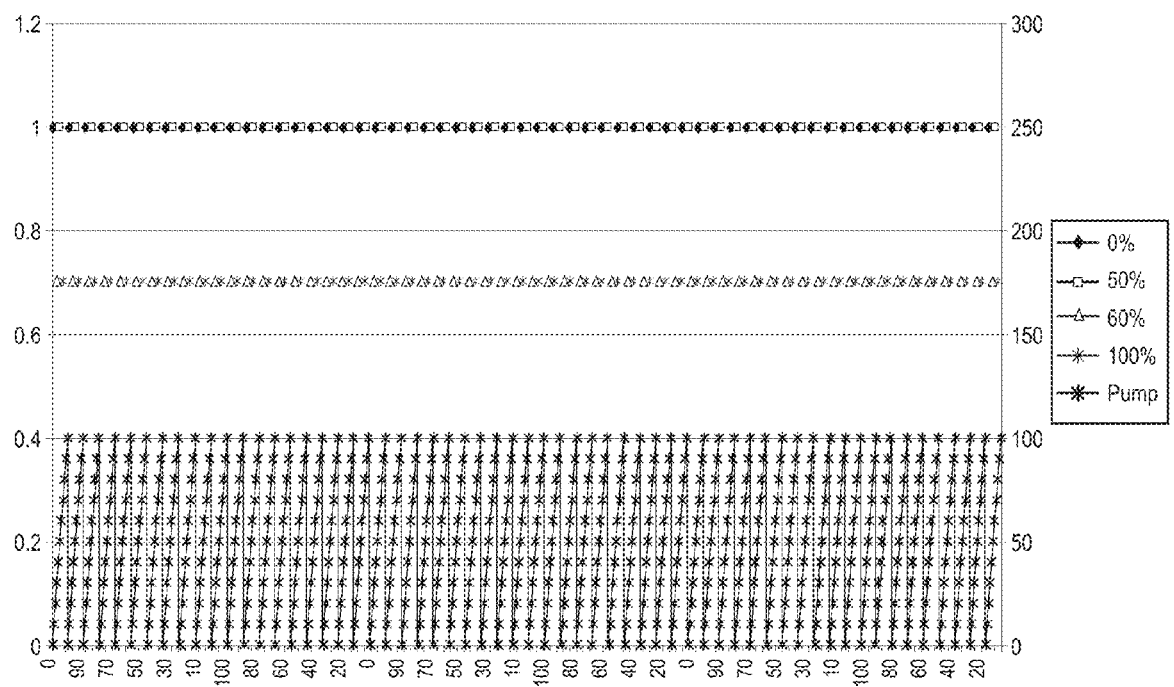
FIG. 15B illustrates a graph illustrating data measurements over a parameter according to various embodiments.

FIG. 15B illustrates the density data displayed using the data collected from the four groups or bins (260, 262, 264, 266 of FIG. 15A) referenced to pump position. Using the bins, the transition from water to oil can be determined, and that it takes placed between 50% and 60% of the piston stroke. The total number of bins can be increased to improve the resolution of the measurement.

Figure 16:
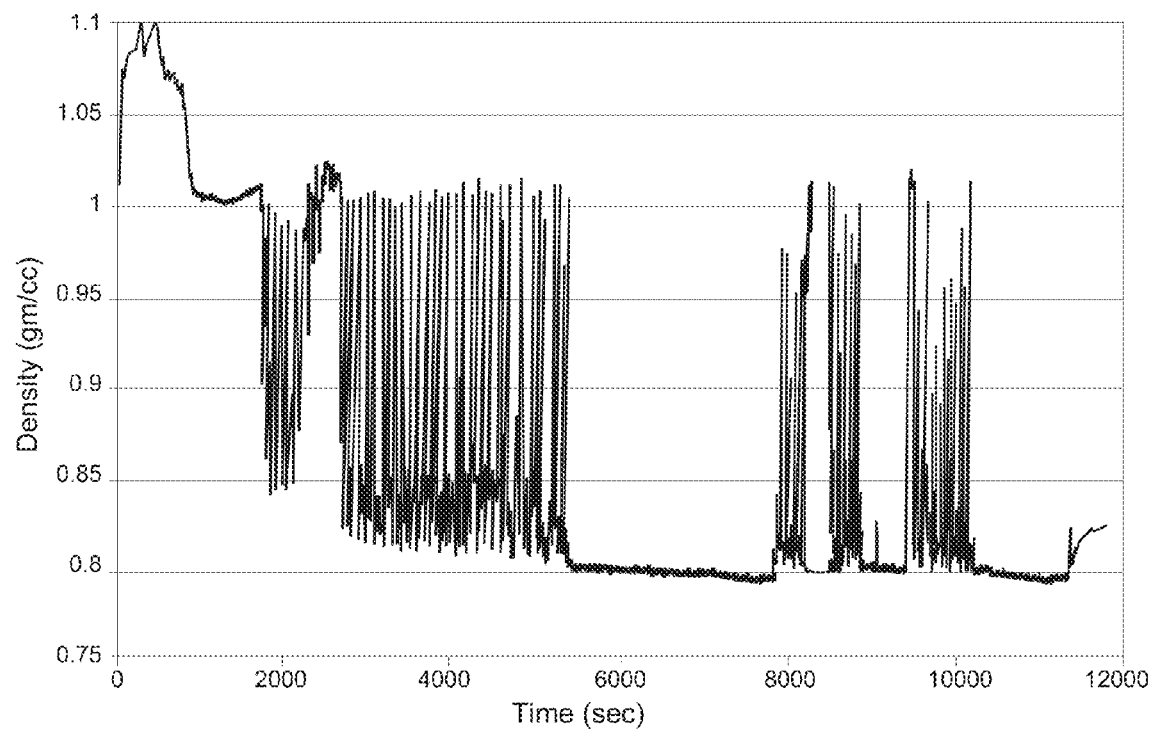
FIG. 16 illustrates a graph illustrating raw data measurements.
Figure 17:
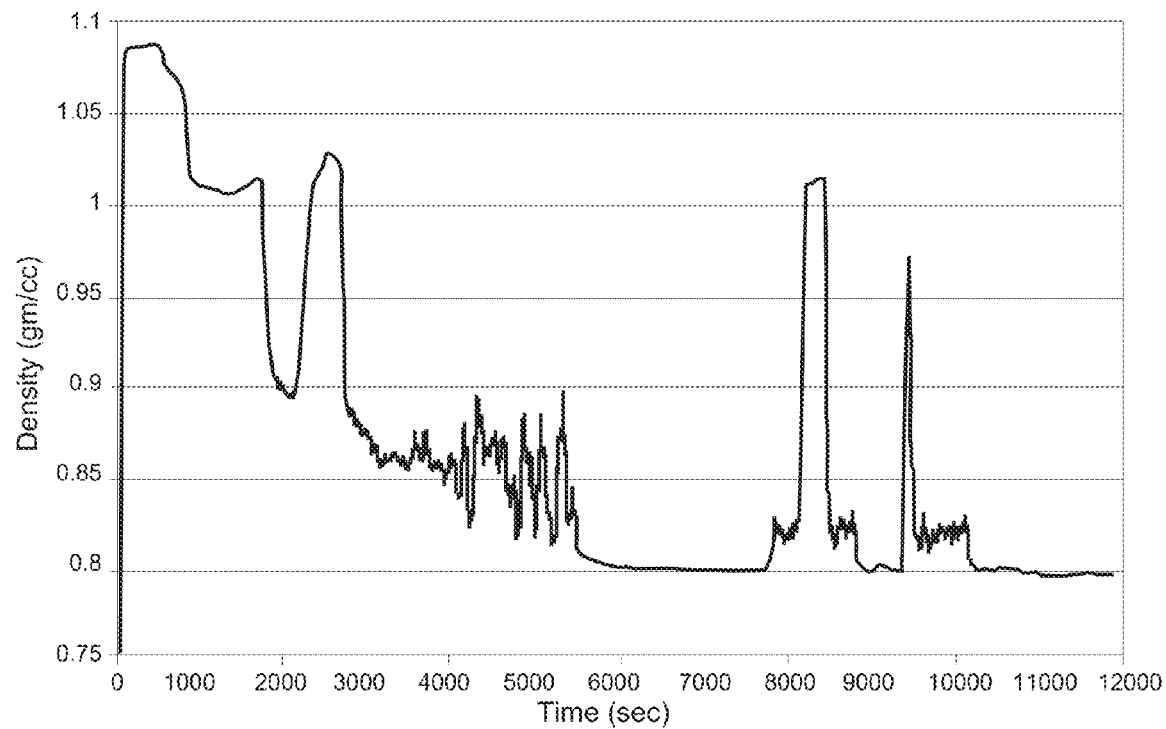
FIG. 17 illustrates a graph illustrating data measurements over a parameter according to various embodiments.

FIG. 16 illustrates raw data taken before the methods herein are used. It is a raw density plot showing the variation seen for a typical pump out for mud/filtrate to oil. In the example shown the density varies from 1.1 g/cc to 0.8 g/cc. FIG. 17 illustrates an example where the weighted average logic of FIG. 9 is applied to the data of FIG. 16, where the analysis of the data creates the weight average curve of FIG. 17.

Figure 18:
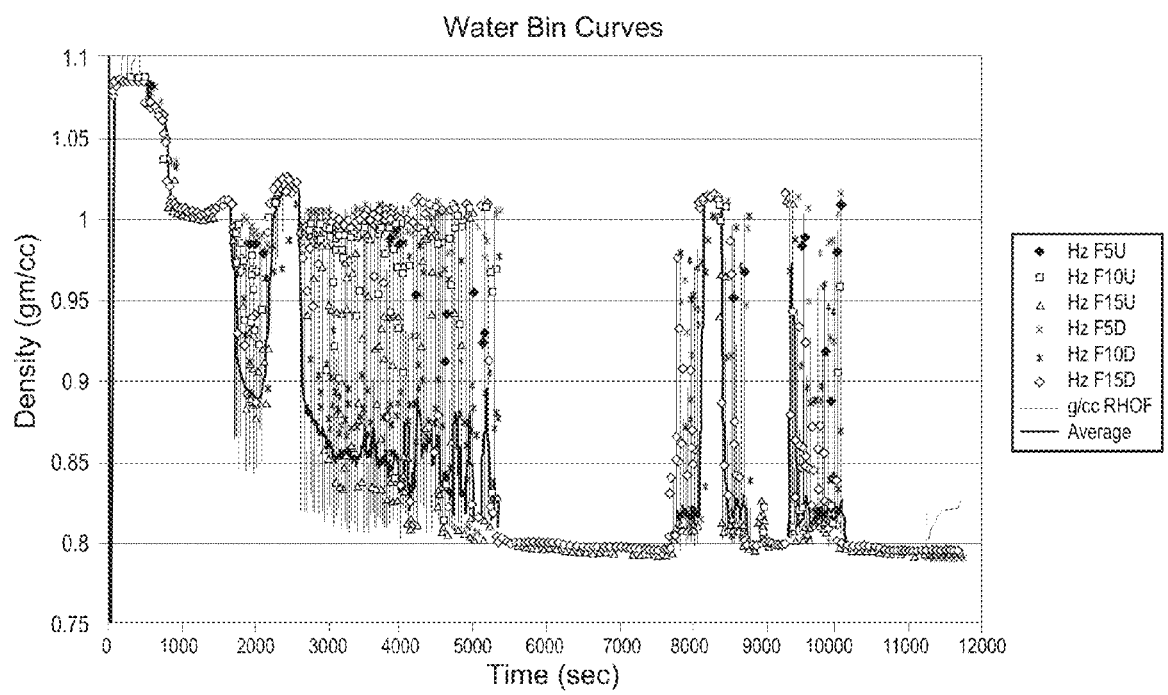
FIG. 18 illustrates a graph illustrating data measurements over a parameter according to various embodiments.
Figure 19A:
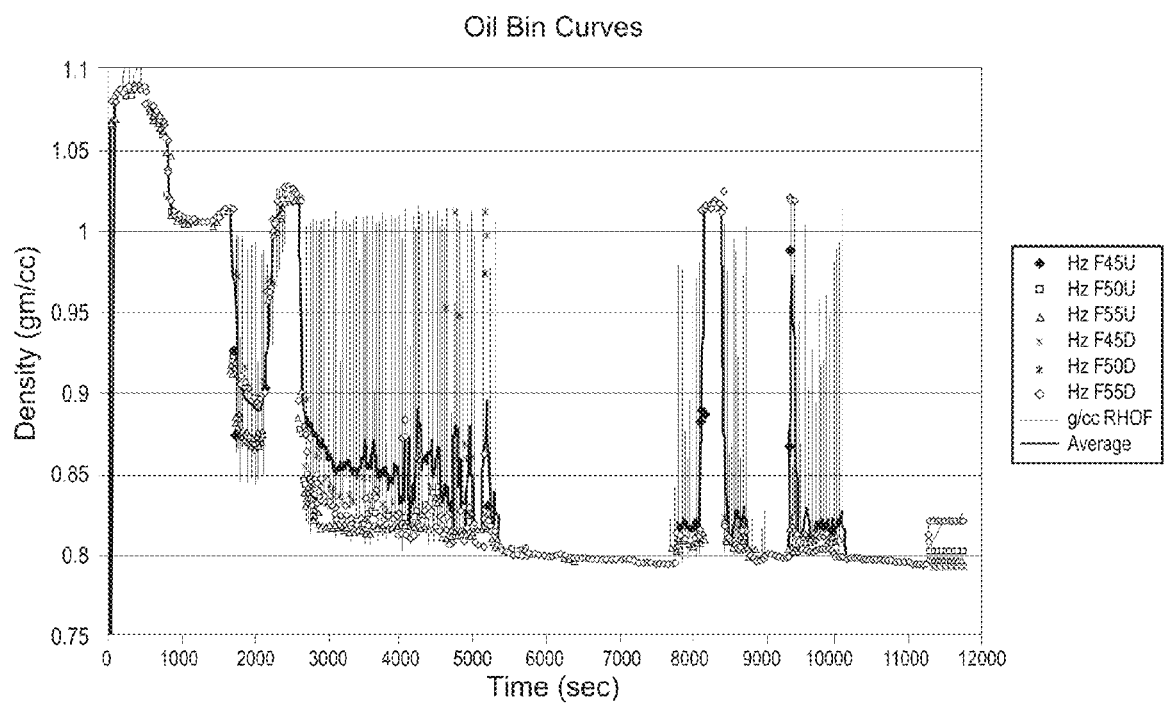
FIGS. 19A-19B illustrates a graph illustrating data measurements over a parameter according to various embodiments.
Figure 19B:
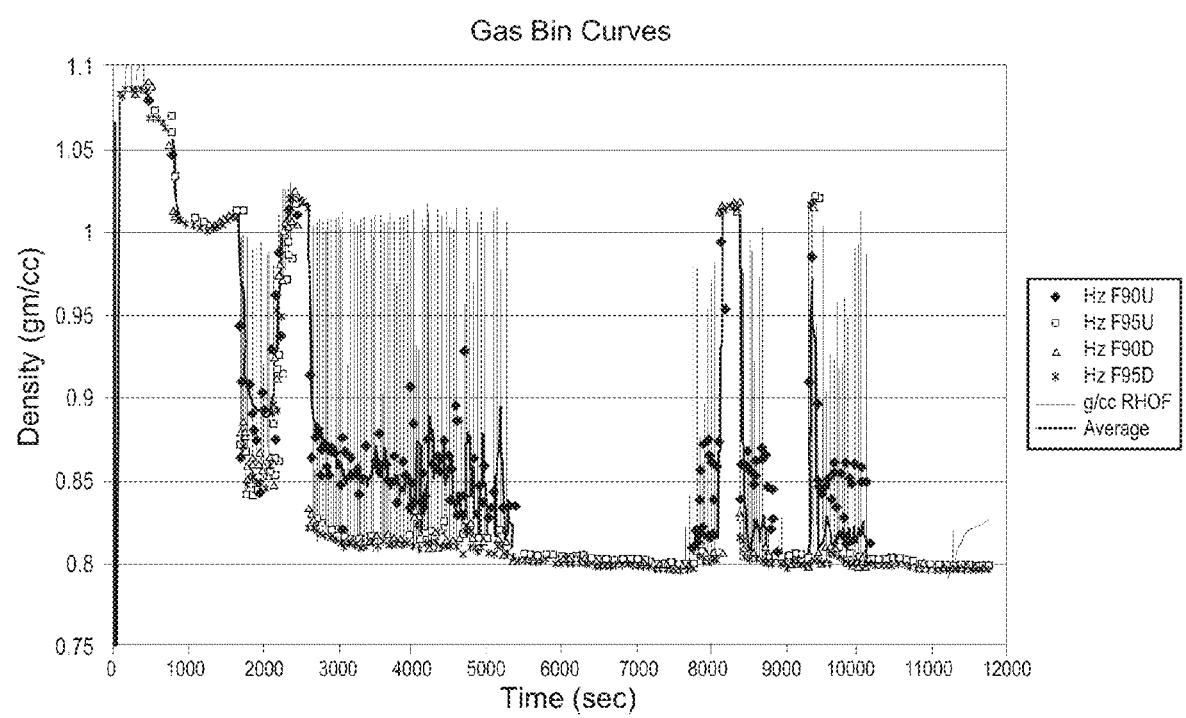

FIGS. 18, 19A and 19B illustrate an analysis of the raw sensor data of FIG. 16, using the method of FIG. 10. In FIG. 18, the equal pump stroke periods create curves showing the fluid distribution related to the pump position in the 0, 5%, 10% and 15% position (up and down strokes). This represents an example of when water would likely be in the grouping or bin. When heterogeneous fluid is present, the binned data is scattered as shown in FIG. 10. When the fluid is homogeneous, the data becomes stacked.

In FIG. 19A, only selected portions of the pump stroke are shown which better represent the formation oil sample being pumped, which in this case are the lighter fluids and uses pump displacement bins of, 45%, 50% and 55% (up and down strokes) In FIG. 19B, the other pump stroke bins are shown which plots the still lighter fluid curves indicating the presence of gas and uses pump displacement bins of 90 and 95% (up and down strokes)

Figure 20:
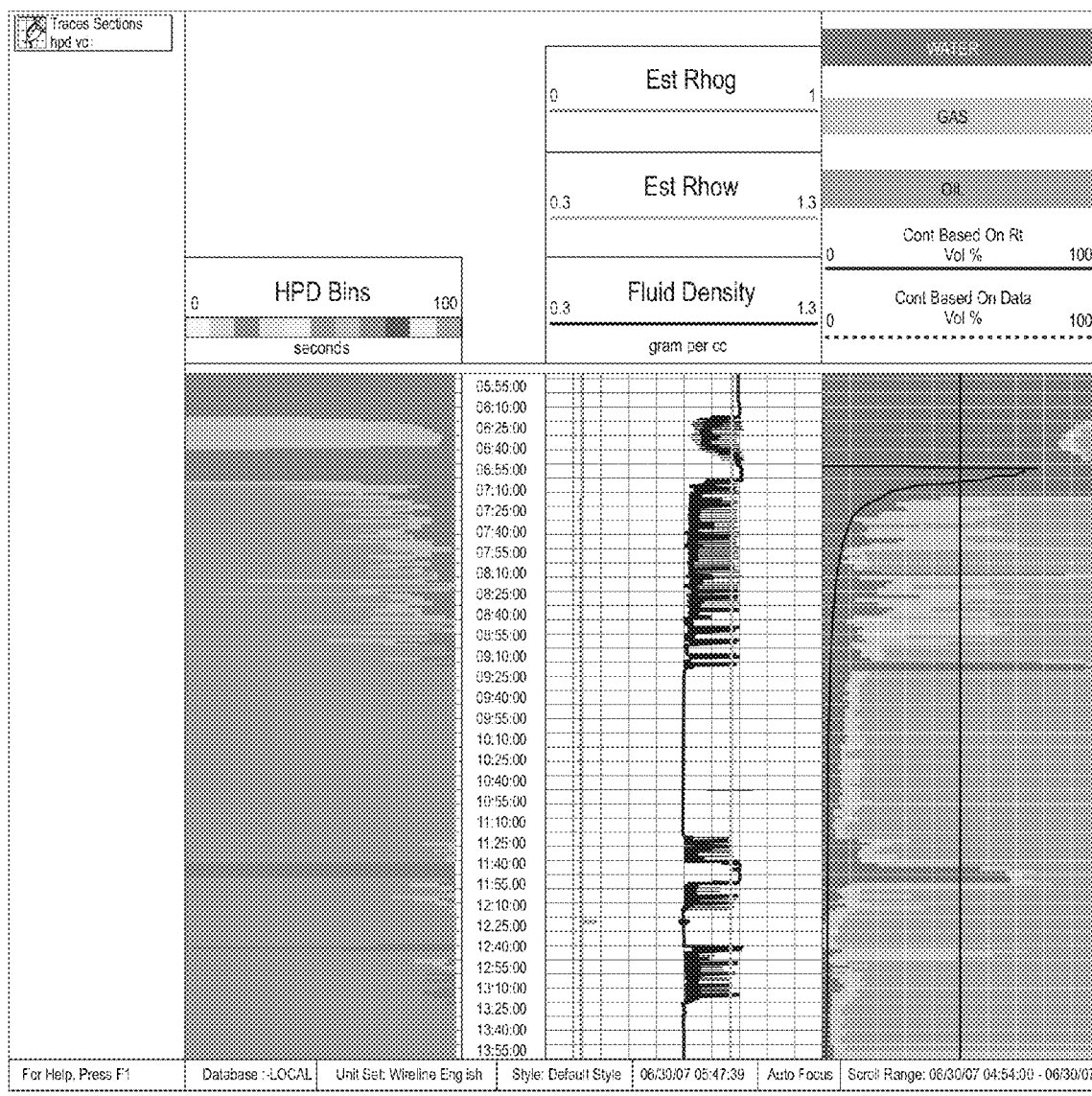
FIG. 20 illustrates a graph illustrating data measurements over a parameter according to various embodiments.

FIG. 20 represents an example of binned curves using the logic in FIG. 11, applied to the density data shown in FIG. 16. This is a plot showing the pump position on one scale divided into equal bins from 0 to 1. Within these bins a color represents the fluid being expelled from the pump at that pump position. As pumping continues the plot is filled in with the shading graphically representing the fluid fractions while pumping stroke by stroke.

Figure 32:
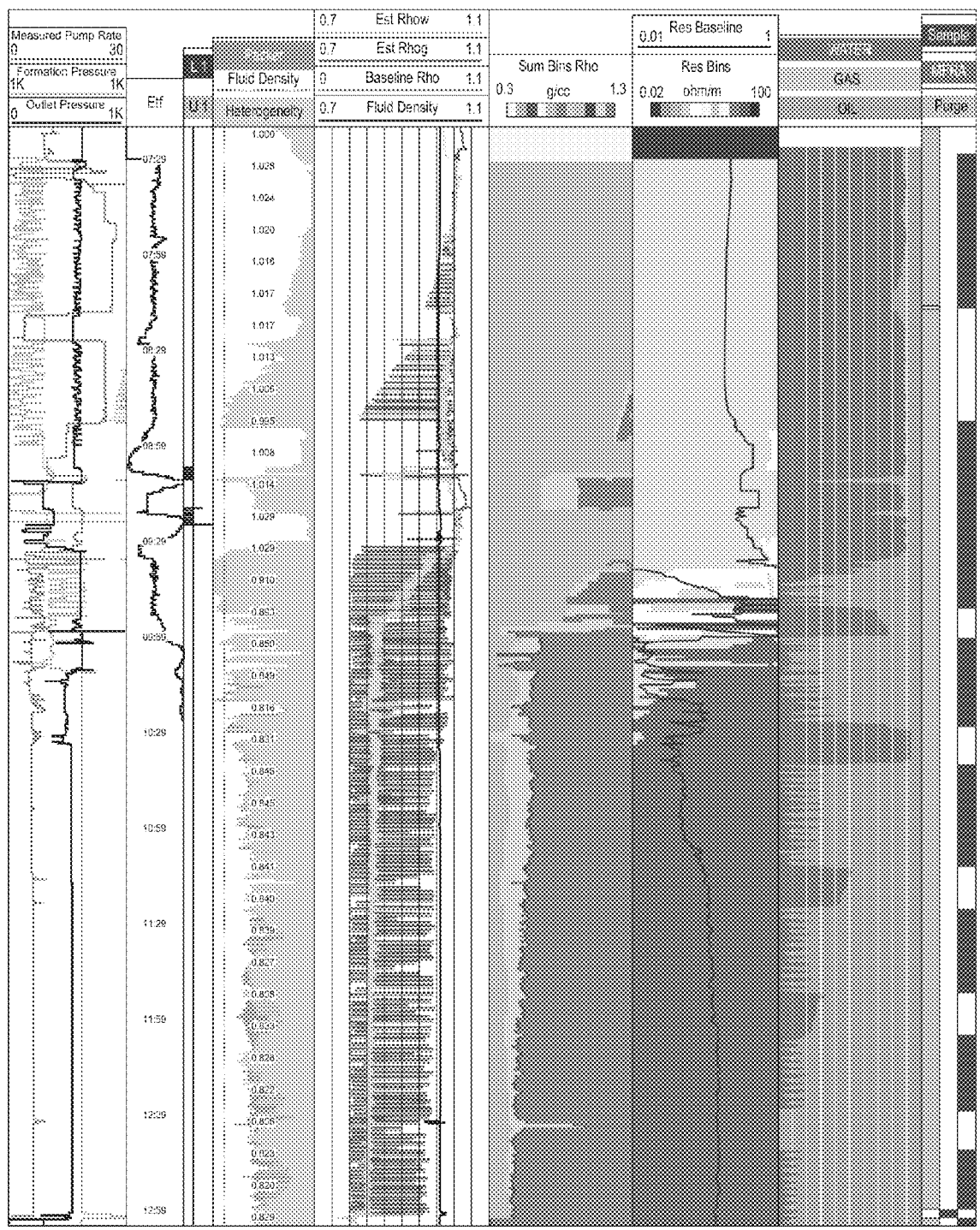
FIG. 32 illustrates a graph illustrating data measurements over a parameter according to various embodiments.

FIG. 32 represents another example of using the logic applied to raw sensor data. The early pump out sensor profile has an initial density that varies around 1.04 g/cc indicating the initial presence of whole mud and fines. The density soon decreases to 1.025 g/cc. The initial resistivity response was 0.23 ohm-m while whole mud and fines were present. The resistivity soon decreases to 0.18 ohm-m, indicating filtrate flowing from the formation. The density data indicates no formation water was present. The water phase density decreases from 1.025 g/cc to 1.02 g/cc indicating that the water present during this time was filtrate rather than formation water. Distilled in situ water density is present and establishes both hydrocarbon indication in many cases and the minimum expected density of water. The first indication of hydrocarbons occurred after 30 liters of fluid was pumped at a flow rate of 25 cc/sec. The measured density fell below the distilled in situ water density value, which was calculated and presented real-time, 0.99 g/cc in this case, confirming some hydrocarbon probability. Review of the fluid density distribution track indicated the relative volume of fluid with hydrocarbon density ranging from 0.9 to 1.0 g/cc was less than 5% until plot time 8:59.

Soon thereafter, the relative volume of fluid with density ranges from 0.8 to 0.9 g/cc increasing to 10%. Taking into account variable pump efficiency, the fluid density distribution track represents 1 liter of pumped volume from left to right and is color coded in bins of 0.1 g/cc and ranging from 0.3 to 1.3 g/cc. A steady cleanup trend from water based mud filtrate to oil is indicated in both the fluid density and resistivity volumetric distribution tracks. A steady clean up trend is also indicated by the change in baseline density from a value above the distilled water cutoff to approximately 0.82 g/cc. The density minima values are nearly constant after the oil volume surpassed 40%. The seemingly erratic 0.25 g/cc variation is expected in an immiscible fluid system. The minima and maxima values represent the densities of the oil and water phases respectively.

The water hold up probability is also determined based on a capacitance measurement and the result is displayed in Water track 8. The water holdup surrounding the capacitance sensor tends to increase when fluid is diverted around the sensor and water settles around the sensor. This no-flow condition is necessary for reducing MRILab T1 fit error and it is indicated by the lack of blue flag shading ("MRFA" Track 9).

Two sequential samples were collected after pumping 13 hours. Prior to delivering the samples to the lab, review of the density data led to volumetric contamination predictions of 12% (sample #2) and 7.6% (sample #2A). The lab reported the first sample #2 was 10% contaminated by weight and sample #2A was 5% contaminated.

Figure 21:
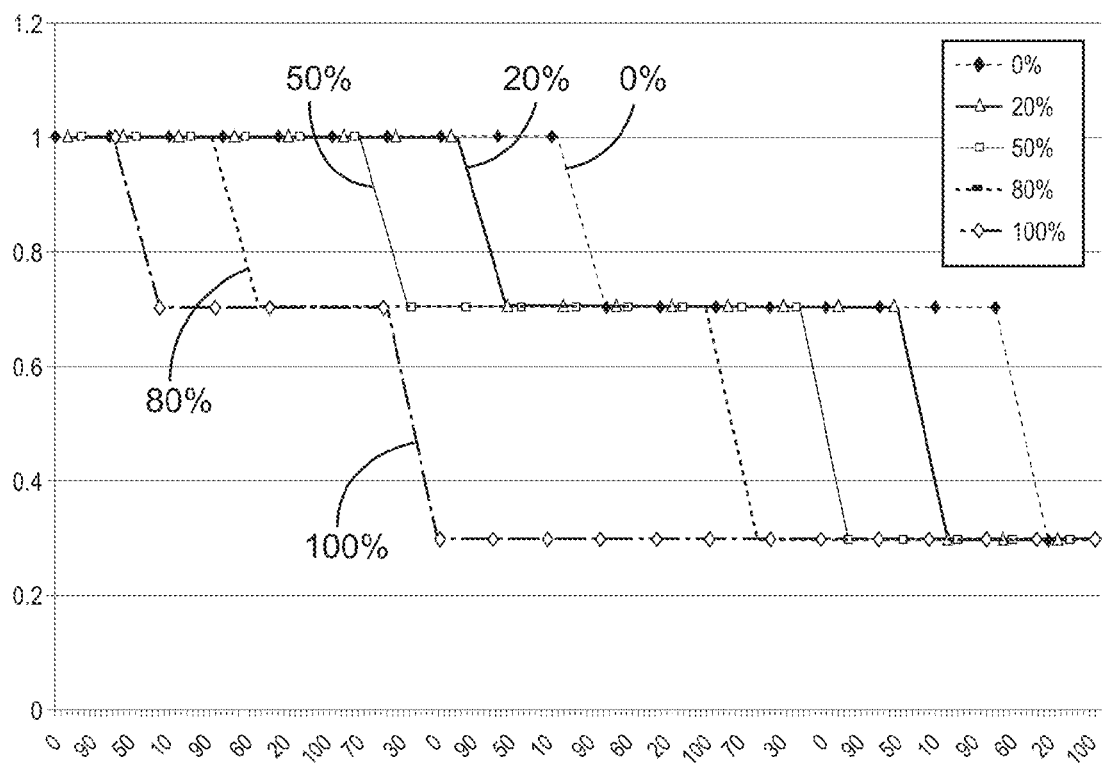
FIG. 21 illustrates a graph illustrating data measurements over a parameter according to various embodiments.

FIG. 21 illustrates another example of a bin method where the value of the density measurements can be correlated to the position of the pump piston. The bins of the pump piston position are the 0%, 20%, 50%, 80%, and 100%, where each of these are plotted in FIG. 21. The individual bin or group indicates the percentage of the cylinder where the measurement is made. Using this method, the density of the water, oil and gas condensate may be measured well before the fluid is 100% clean. By looking at the transition between water to oil, a volumetric estimation can be determined considering what percentage the bin indicates a specific density. In addition, heterogeneity can be determined.

Figure 22:
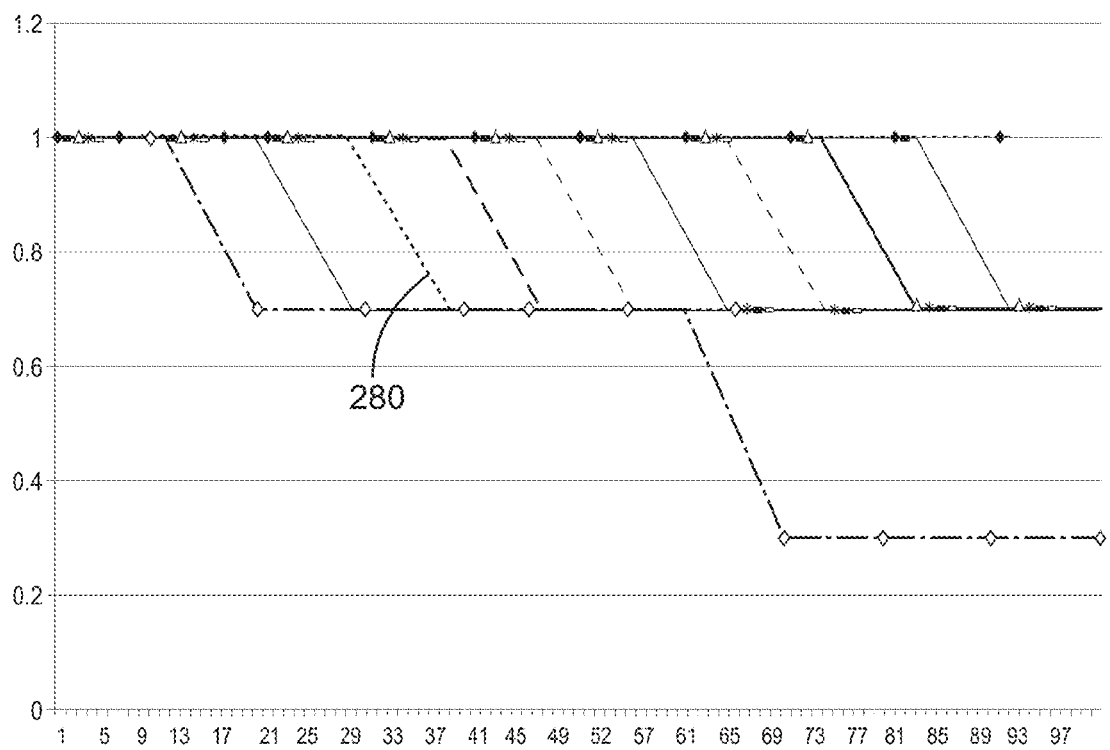
FIG. 22 illustrates a graph illustrating data measurements over a parameter according to various embodiments.

In an option, the sensor will depend on which bins are used for measurements. The 0% bin which makes the measurement of the first fluid that leaves the cylinder will have the greatest density fluid, this bin would be best suited to make the water phase measurement and may set the 100% contaminated point of the sample fluid. Using the same method, the most reliable gas condensate or early stage oil measurements would be made by the 100% bin. As can be seen, the 100% bin showed the first showing of oil and as the contamination in the cylinder reduced more and more bins confirmed the existence of oil. The example shown in FIG. 21 shows a gas condensate sample as all the bins cleaned up to 100% gas condensate. FIG. 22 shows the water bin 280 never transitioning to a lighter fluid. In a contaminated system, there may always be some level of contamination, depending on the fluid being sampled, and there may not be any indication of gas. If at any point, all or a large percentage of the bins read the same value, the fluid can then be determined to be homogenous fluid of the same fluid properties.

Figure 23:
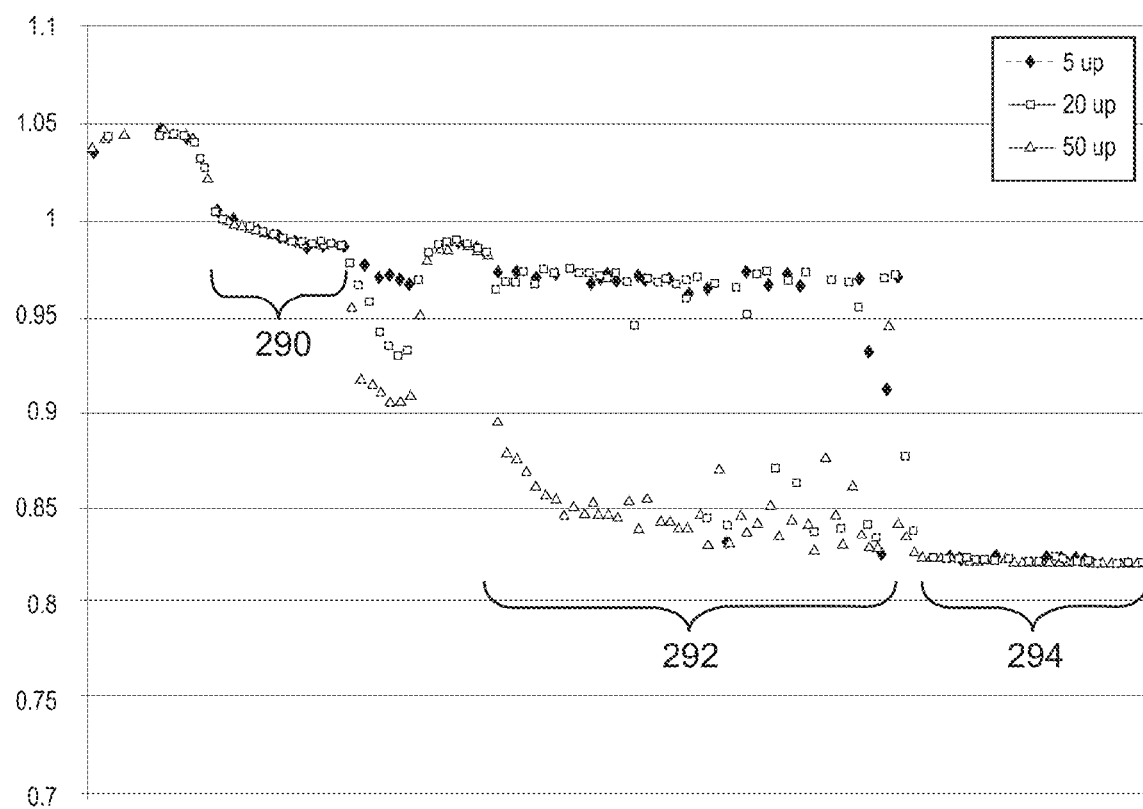
FIG. 23 illustrates a graph illustrating data measurements over a parameter according to various embodiments.

FIG. 23 is an example of a plotted data using the methods herein, showing a fluid sample transitioning from a density of 1.05 g/cc to 0.83 g/cc. The data measurements are binned or grouped into three bins based on piston stroke. At 290, there is a transition to water. At 292, the bin having the 50% stroke position has oil. At 294, all of the bins are measuring oil. When the bin density separates, it can be assumed the fluids are heterogeneous and analysis of the bin volumes may enable a mixing or heterogeneity index to be calculated. This measurement can also be made in a time base where the sample rate is determined by the velocity and or rate of the fluid.

Figure 30:
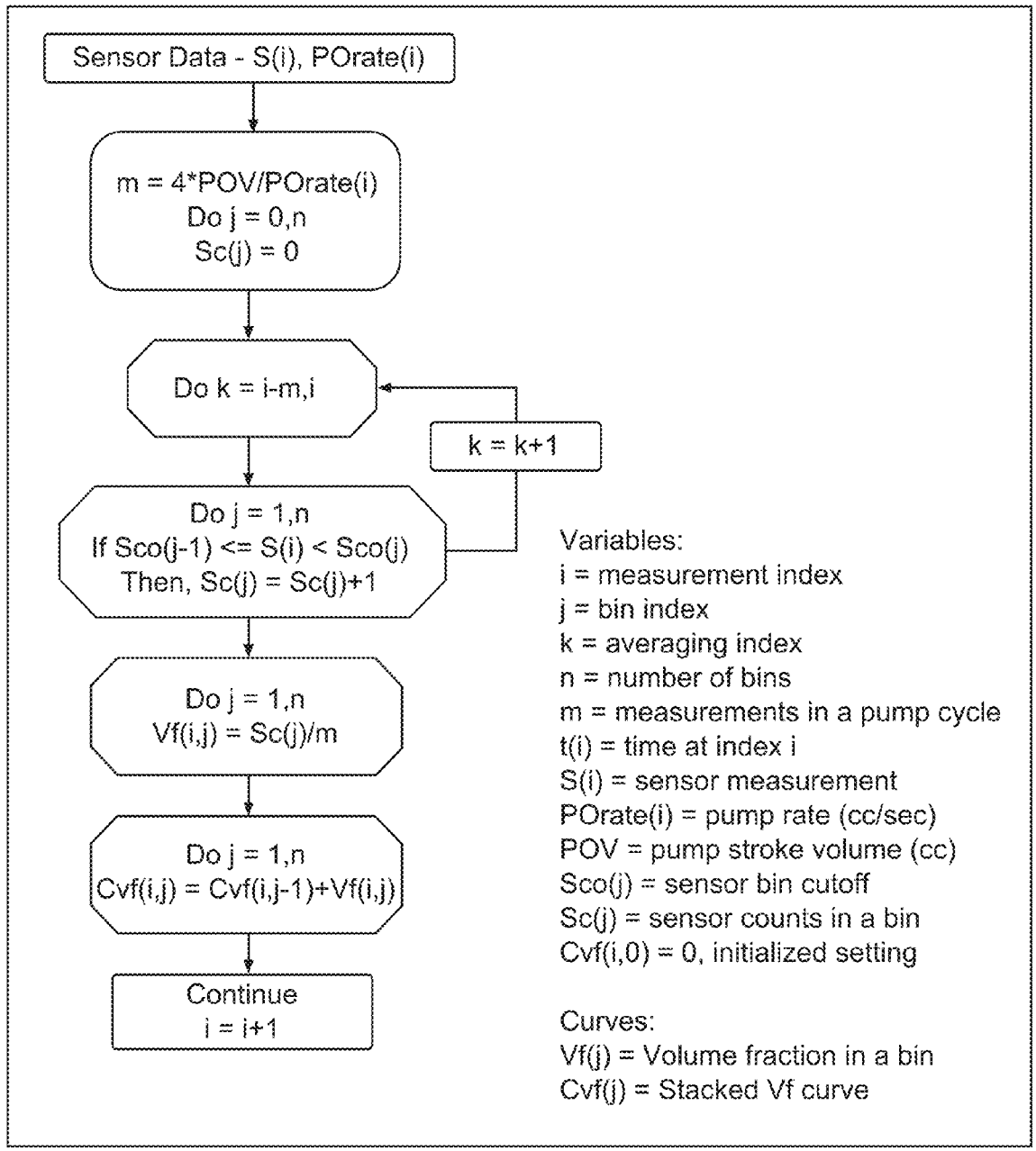
FIG. 30 illustrates a method flow diagram according to various embodiments.
Figure 31:
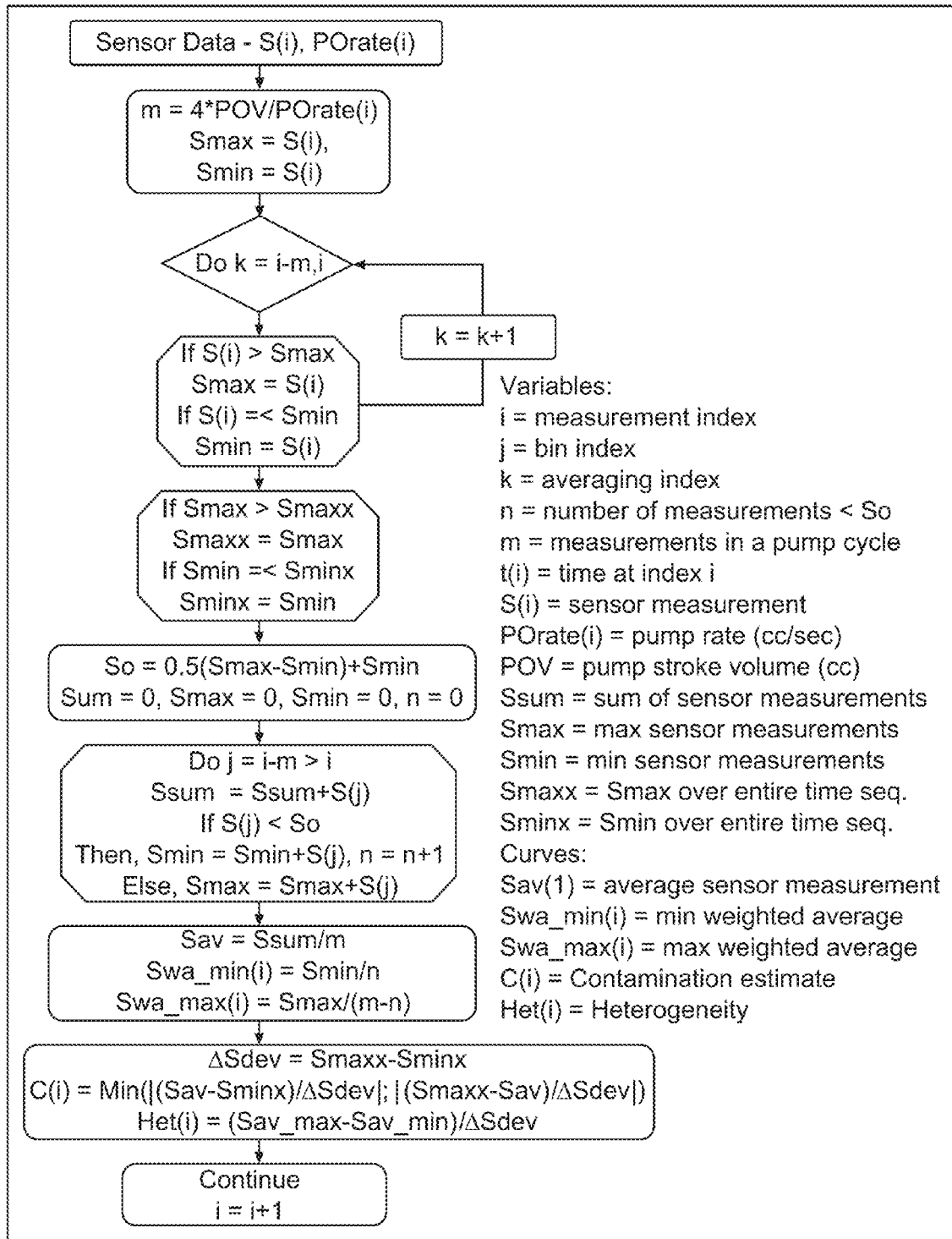
FIG. 31 illustrates a method flow diagram according to various embodiments.

FIGS. 30 and 31 illustrate a flow diagram showing an example of logic that can be used to create volume fraction curves from fluid sensor readings. In both FIGS. 30 and 31, one pump stroke cycle is used for determining the volume fractions because the pump tends to induce the variations in the sensor measurements and fluid phases, as discussed above. Using a pump stroke cycle is not a limitation of this method, however. Any amount of either volume of time can be used.

In FIG. 30, volume fractions are based on fixed cutoff levels that are equally spaced intervals of the sensor readings (i.e. 0.1, 0.2, 0.3, 0.4 . . . 1.0). These intervals or bins can also be assigned colors that characterize the type of fluids expected within the bins. The intervals or bins may or may not be equally spaced. The spacing depends on the sensor property being measured and the relationship it has to the volume fractions or different fluid types or phases. Based on the number of cutoffs or bins, n, a number of volume fraction curves are developed by counting the readings that fall between the cutoffs and the dividing them by the total number of readings during a pump stroke, m. The stacked volume fraction curves can be plotted in a single track with the spacing between the curves representing the volume fraction of each binned flow component. The spaces between the curves can be shaded to represent the fluid types.

Weight average curves are developed based on a floating cutoff with the logic shown in FIG. 31. The sensor data, such as density, is scanned during a pump stroke to determine the maximum and minimum reading detected ($S_{max}$, $S_{min}$). A fraction between the $S_{max}$ and $S_{min}$ is chosen to determine how to create the weighted average over the pump stroke (usually 50%). Readings above this floating cutoff are summed and averaged to determine a curve that is weighted to the higher measurements and another curve weighted to lower measurements. The simple average of the sensor reading is also determined over the volume to time interval chosen.

In FIG. 31, the logic is shown for determining maximum and minimum of the sensor measurements over the pumping sequence, such as the entire sequence ($S_{maxx}$, $S_{minx}$). The $S_{maxx}$ and $S_{minx}$ represent the sensor measurement extremes of the sensor measurement, which can be either the filtrate or formation fluids. As the $S_{av}$ approaches either of these extremes, this is an indication of cleanup. To estimate the contamination the difference between the sensor average, $S_{av}$, and the extremes is determined and divided by the difference between the sensor extremes. The minimum of the two estimates is the contamination estimate over the volume or time interval C(i) as shown in FIG. 31.

The weighted volume fraction curves can be used to estimate the heterogeneity of the flow, as further discussed above. This heterogeneity curve Het(i) is the difference between the weighted volume fraction curves divided by the difference between the sensor extremes over the entire sampling sequence. The heterogeneity curve is a measure of how well the fluids are mixed and which normally converges when cleanup occurs.

Implementing the apparatus, systems, and methods of various embodiments may provide the ability to determine fluid types and heterogeneity with greater accuracy than was previously achieved.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

What is claimed is:

1. A method for sampling formation fluid, the method comprising:
    introducing formation fluid into a pump, the pump having a pump piston, an inlet, and an outlet;
    segregating the fluid within the pump;
    pumping the fluid out through a flowline by action of the pump;
    sensing the fluid with a fluid sensor at or downstream of the outlet of the pump to obtain sensor data;
    operating on the sensor data using a processor to identify a fluid type correlated to position of the pump piston; and
    selectively opening and closing a valve to accept a desired fluid into at least one sample chamber based on the sensor data correlated to the position of the pump piston and the fluid type, wherein the valve is opened and closed during the pumping.

2. The method as recited in claim 1, wherein the valve is selectively opened and closed to accept a first fluid type into a first sample chamber, and to accept a second fluid type into a second sample chamber.

3. The method as recited in claim 1, wherein the sensing includes sensing a density of the fluid.

4. The method as recited in claim 1, wherein the method is performed until at least one sample chamber is filled.

5. The method as recited in claim 1, wherein the method includes obtaining sensor data correlated to position of the pump piston in terms of fractions of pump displacement.

6. The method as recited in claim 1, wherein the pump assists in segregating the fluid.

* * * * *